US012648813B2

(12) United States Patent
Pyun et al.

(10) Patent No.: US 12,648,813 B2
(45) Date of Patent: Jun. 9, 2026

(54) DIAGNOSTIC DEVICE WITH PROBE INCLUDING CAMERA

(71) Applicant: SPECLIPSE, INC., Gyeonggi-do (KR)

(72) Inventors: Sung Hyun Pyun, Seoul (KR); Wan Ki Min, Gyeonggi-do (KR)

(73) Assignee: SPECLIPSE, INC., Gyeonggi-do (KR)

( * ) Notice: Subject to any disclaimer, the term of this patent is extended or adjusted under 35 U.S.C. 154(b) by 303 days.

(21) Appl. No.: 18/065,792

(22) Filed: Dec. 14, 2022

(65) Prior Publication Data

US 2024/0148436 A1     May 9, 2024

(30) Foreign Application Priority Data

Nov. 7, 2022     (KR) ........................ 10-2022-0147038

(51) Int. Cl.
A61B 18/20        (2006.01)
A61B 5/00         (2006.01)
(Continued)

(52) U.S. Cl.
CPC ............ A61B 18/20 (2013.01); A61B 5/0075 (2013.01); A61B 5/0082 (2013.01); A61B 90/361 (2016.02); A61B 90/37 (2016.02); A61B 2018/00577 (2013.01); A61B 2018/00696 (2013.01)

(58) Field of Classification Search
None
See application file for complete search history.

(56) References Cited

U.S. PATENT DOCUMENTS

2018/0271502 A1* 9/2018 Zarrine-Afsar ...... A61B 5/0095
2020/0300702 A1* 9/2020 Pyun .......................... B63J 2/14
(Continued)

FOREIGN PATENT DOCUMENTS

JP          2017099603 A       6/2017
KR     1020170114973 A      10/2017
(Continued)

OTHER PUBLICATIONS

Extended European Search Report from corresponding European Patent Application No. EP 22213413.2, dated Aug. 16, 2023.
(Continued)

*Primary Examiner* — Ankit D Tejani
(74) *Attorney, Agent, or Firm* — Harness, Dickey & Pierce, PLC

(57)                ABSTRACT
Provided is a method including radiating first guide light, which guides a radiation position of a first pulsed beam, onto a suspicious tissue, receiving a first user input for instructing an output of the first pulsed beam while the first guide light is radiated, applying the first pulsed beam to the suspicious tissue to induce plasma ablation in a first target region corresponding to the radiation point of the first guide light, in response to the first user input, wherein the applying of the first pulsed beam is performed after obtaining first image data obtained by capturing an image of the first guide light and a tissue in a periphery the first guide light while the first guide light is radiated to the suspicious tissue, and obtaining target spectrum data on the plasma ablation, obtaining first disease information, and displaying the first image data and the first disease information.

7 Claims, 21 Drawing Sheets

(51) Int. Cl.
      *A61B 90/00*          (2016.01)
      *A61B 18/00*          (2006.01)

(56)                    References Cited

U.S. PATENT DOCUMENTS

| | | |
|---|---|---|
| 2021/0094667 A1 | 4/2021 | Pyun et al. |
| 2021/0128939 A1 | 5/2021 | Verghese et al. |
| 2022/0346875 A1 | 11/2022 | Khan et al. |

FOREIGN PATENT DOCUMENTS

| | | |
|---|---|---|
| KR | 1020170125310 A | 11/2017 |
| KR | 1020190058970 A | 5/2019 |
| KR | 1020200112602 A | 10/2020 |
| WO | WO-2022/032211 A1 | 2/2022 |

OTHER PUBLICATIONS

Decision to Grant from corresponding Korean Patent Application No. 9-5-2025-054073800, dated Jun. 9, 2025.

* cited by examiner

10

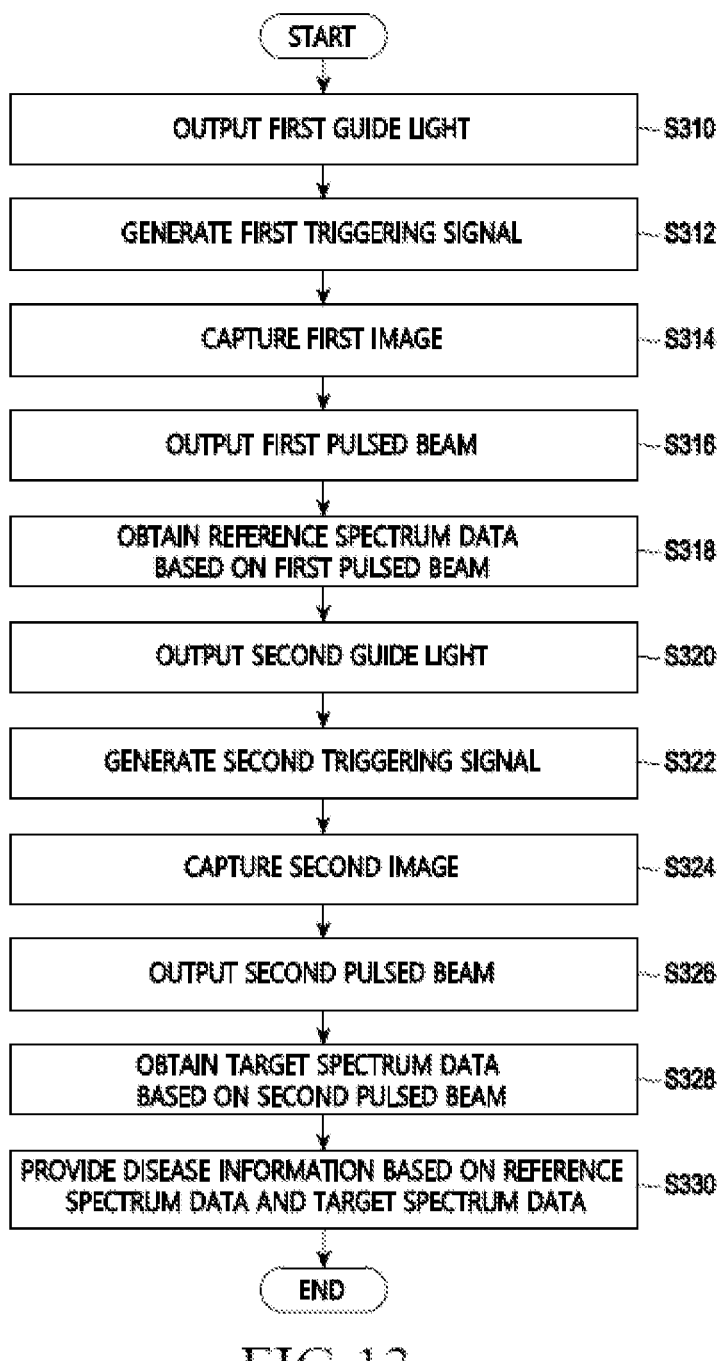

START

OUTPUT FIRST GUIDE LIGHT — S310

GENERATE FIRST TRIGGERING SIGNAL — S312

CAPTURE FIRST IMAGE — S314

OUTPUT FIRST PULSED BEAM — S316

OBTAIN REFERENCE SPECTRUM DATA BASED ON FIRST PULSED BEAM — S318

OUTPUT SECOND GUIDE LIGHT — S320

GENERATE SECOND TRIGGERING SIGNAL — S322

CAPTURE SECOND IMAGE — S324

OUTPUT SECOND PULSED BEAM — S326

OBTAIN TARGET SPECTRUM DATA BASED ON SECOND PULSED BEAM — S328

PROVIDE DISEASE INFORMATION BASED ON REFERENCE SPECTRUM DATA AND TARGET SPECTRUM DATA — S330

END

FIG.13

DIAGNOSTIC DEVICE WITH PROBE INCLUDING CAMERA

CROSS-REFERENCE TO RELATED APPLICATION

This application claims priority to and the benefit of Korean Patent Application No. 10-2022-0147038, filed on Nov. 7, 2022, the disclosure of which is incorporated herein by reference in its entirety.

FIELD

The present disclosure relates to a laser diagnostic device having a camera mounted on a probe using a spectroscopic analysis method, and more particularly, to a disease information providing method of confirming a radiation position of a pulsed beam with the naked eye and providing disease information according to the radiation position, and a device for performing the same.

BACKGROUND

As conventional disease diagnosis using laser spectroscopic analysis, for example, Raman spectroscopy (RS) or laser-induced breakdown spectroscopy (LIBS) is used.

However, since a spot size of a laser is significantly smaller than an object of laser radiation in a conventional technique, there is a problem in that different diagnosis results are obtained even for the same object depending on a laser radiation position, and the laser radiation position on the object cannot be clearly identified.

SUMMARY

The present disclosure is directed to providing a disease information providing method in which pieces of spectrum data related to a plurality of pulsed beams, which are radiated onto the same object, are comprehensively considered.

The present disclosure is also directed to improving the accuracy of disease information by clearly identifying a radiation position of a pulsed beam, and obtaining and comparing different pieces of spectrum data on the same object.

According to an aspect of the present disclosure, there is provided a disease information providing method including radiating first guide light, which guides a radiation position of a first pulsed beam, onto a suspicious tissue, receiving a first user input for instructing an output of the first pulsed beam while the first guide light is radiated, applying the first pulsed beam onto the suspicious tissue to induce plasma ablation in a first target region corresponding to the radiation point of the first guide light, in response to the first user input, wherein the applying of the first pulsed beam is performed after obtaining first image data obtained by capturing an image of the first guide light and a tissue in a periphery the first guide light while the first guide light is radiated to the suspicious tissue, obtaining target spectrum data on the plasma ablation, obtaining first disease information related to the first target on the basis of the first spectrum data, and displaying the first image data and the first disease information.

According to another aspect of the present disclosure, there is provided a disease information providing device including a laser generating unit configured to generate a pulsed beam, a housing configured to accommodate the laser generating unit and including an opening providing a radiation path of the pulsed beam, a guide tip provided near the opening and configured to adjust a radiation distance of the pulsed beam from a target to a laser generating module by being in contact with the target, a light receiving module disposed adjacent to the opening or the guide tip and is configured to receive plasma light induced when the pulsed beam is radiated to the target, a guide module disposed inside the housing and is configured to radiate guide light visually displaying a radiation position of the pulsed beam, an imaging module disposed in parallel with the light receiving module and is configured to capture an image of the radiation position of the pulsed beam and a predetermined region near the radiation position, a switch module disposed on at least a part of an outer surface of the housing, and configured to trigger operations of the imaging module and the laser generating unit in response to a user input, and a processor configured to control operations of the laser generating module and the imaging module, wherein the processor is configured to, when the user input is applied to the switch module, transmit, to the imaging module, a first signal for instructing to capture an image of the guide light pointing at a radiation spot of the pulsed beam while the guide light is radiated, and after the first signal is transmitted, transmit a second signal for instructing the radiation of the pulsed beam to the target.

BRIEF DESCRIPTION OF THE DRAWINGS

The above and other objects, features, and advantages of the present disclosure will become more apparent to those of ordinary skill in the art by describing exemplary embodiments thereof in detail with reference to the accompanying drawings, in which:

FIG. 13 is a flowchart of a disease information providing method according to another embodiment;

DETAILED DESCRIPTION OF EXEMPLARY EMBODIMENTS

Figure 1:
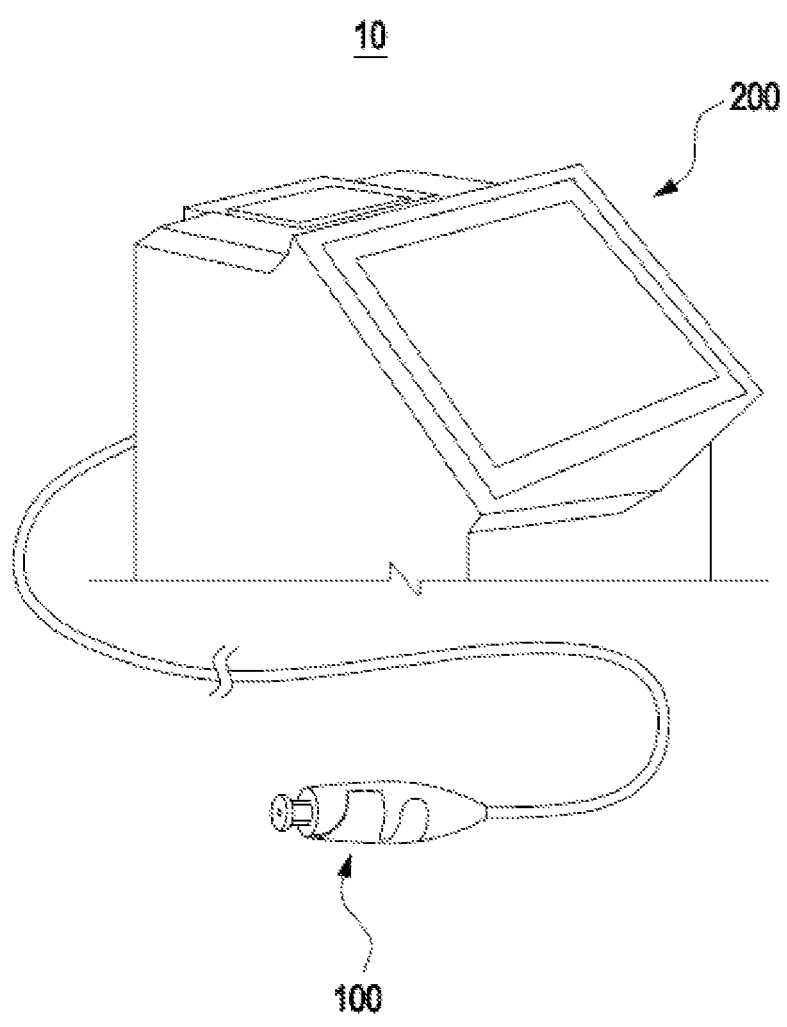
FIG. 1 is a block diagram illustrating a diagnostic system according to one embodiment of the present specification.

The above and other objectives, features, and advantages of the present disclosure will become more apparent from the following description with reference to the accompanying drawings. However, the present disclosure may be modified into various forms and may have a variety of embodiments, and, therefore, specific embodiments will be illustrated in the drawings and described in detail below.

The embodiments described herein are intended to clearly describe the spirit of the present disclosure to those skilled in the art to which the present disclosure pertains, and thus the present disclosure is not limited to the embodiments described herein, and the scope of the present disclosure should be construed as including alternations or modifications without departing from the spirit of the present disclosure.

The drawings accompanying the present specification are provided to easily describe the present disclosure, and shapes shown in the drawings may be illustrated with exaggeration as necessary to help understanding of the present disclosure, and thus the present disclosure is not limited to the drawings.

When a detailed description of a known function or configuration related to the present disclosure is determined to unnecessarily obscure the gist of the present disclosure, the detailed description thereof will be omitted herein. In addition, numerical terms (e.g., "first," "second," and the like) used in the description of the present specification are merely identification symbols for distinguishing one component from another component.

In addition, suffixes "unit," "module," and "part" for components used in the following description are given or interchanged in consideration only of convenience of description, and thus these suffixes do not have distinctive meanings or functions.

According to various embodiments, provided are a diagnostic method using laser-induced breakdown spectroscopy and a diagnostic device for performing the same.

The laser-induced breakdown spectroscopy (hereinafter, referred to as "LIBS") is a technique of radiating a short pulsed laser of high power to a target, to be diagnosed to form plasma and performing spectroscopic analysis of light generated from the plasma.

By analyzing electromagnetic waves radiated from the plasma, a composition or state of a material can be identified. In the LIBS, plasma is induced by radiating a laser to a target to be examined, and a spectrum of light generated by the plasma is analyzed, thereby examining characteristics of the target such as a state or composition of the target. Hereinafter, the spectrum may refer to an indicator capable of indicating a nature or characteristic of light. For example, the spectrum may be expressed as a quantity of light for each wavelength, an intensity of the light, or energy of the light.

Hereinafter, a target to which a laser is radiated, that is, a target of the LIBS will be referred to as a "specimen." That is, in the following description, "specimen" may refer to an object that is a target of spectrum analysis. Accordingly, the "specimen" may be understood as an object to which a laser is radiated in an LIBS process.

In general, in the present specification, the specimen may be an object of diagnosis, that is, a target of diagnosis or examination, but the target of spectrum analysis does not necessarily coincide with the target of diagnosis. For example, the specimen may include an object that undergoes LIBS for comparison with the target of diagnosis. Thus, the specimen is not limited to the object of diagnosis, but should be understood as a comprehensive meaning encompassing all targets of spectrum analysis.

In the present specification, various objects may be the specimen. For example, when disease diagnosis or the like is performed on a patient, the specimen may be a part of a component constituting a body of the patient in addition to skin, internal and external tissues, various cells, blood, saliva, and the like. In addition, when diagnosis is to be performed on various non-biological materials in addition to medicines, the specimen may include various materials such as metals or nonmetals, inorganic materials, and the like. In other words, in the present specification, the specimen should be understood as a comprehensive concept including any material that is a target of spectrum analysis.

In addition, in the present specification, "diagnosis" has a comprehensive concept including determination of a characteristic such as a state or a composition of an object to be analyzed using LIBS, and second determination on the basis of the characteristic determination. As an example, the diagnosis may include analysis of a composition of a specific material. As another example, the diagnosis may include not only determination of specific information on the analysis target, such as a nature, a characteristic, and the like of the specimen, but also determination of a disease of a patient or determination of similarity between a previously analyzed specimen and a newly analyzed specimen. As a specific example, in the present specification, the diagnosis using LIBS may be used to determine whether a human body has a disease or an illness, or to obtain biometric information such as a specific cell content, skin age, or a harmful substance content of the human body.

Hereinafter, a diagnostic system 10 according to one embodiment of the present specification will be described with reference to FIGS. 1 to 4.

The diagnostic system 10 according to one embodiment of the present specification is a system configured to perform diagnosis on a specimen using LIBS.

FIG. 1 is a block diagram of the diagnostic system 10 according to one embodiment of the present specification.

Referring to FIG. 1, the diagnostic system 10 may include a laser device 100 and an analysis device 200. In the diagnostic system 10, the laser device 100 may radiate a laser to a specimen to form plasma and may obtain spectrum data from the plasma, and the analysis device 200 may provide disease information on a diagnostic target on the basis of the spectrum data obtained by the laser device 100.

The laser device 100 may radiate a pulsed beam to the specimen. Plasma ablation may be generated in the specimen to which the pulsed beam is radiated. In this case, plasma may be formed in the specimen in which the plasma ablation is generated. That is, the laser device 100 may form the plasma by radiating the pulsed beam to the specimen to induce the plasma ablation in the specimen.

The laser device 100 may collect light from the outside of the laser device. Here, the light collected by the laser device 100 may include laser-derived light that is derived from the pulsed beam radiated to the specimen, and light generated due to the plasma ablation induced in the specimen. The laser-derived light may include reflected light, scattered light, and fluorescent light due to the laser radiated to the specimen. The light generated due to the plasma ablation may include light according to plasma emission and light according to element specific emission.

The laser device 100 may transmit the light collected from the outside to the analysis device 200. As will be described below, the laser device 100 may be optically connected to the analysis device 200, and may transmit the laser-derived light and the light generated due to the plasma ablation to the analysis device 200.

The laser device 100 may obtain the spectrum data by spectroscopically analyzing the collected light. Here, the spectrum data may include information on a spectrum of the light. Specifically, the spectrum data may include data on an intensity measured for each wavelength of the light. Here, the spectrum data may include data obtained by sampling and quantifying the spectrum of the light. For example, when the laser device 100 spectroscopically divides the collected light to measure an intensity for each wavelength for a predetermined period of time, the spectrum data may include a set of intensity values proportional to measured light amount. In the present specification, the spectrum data may be obtained by spectroscopically dividing the light collected by the laser device 100, and accordingly, the spectrum data may have a specific wavelength range according to a configuration for spectroscopically dividing the light or detecting the light. The analysis apparatus 200 may provide disease information by using the obtained spectrum data.

The analysis device 200 may provide the disease information on the basis of the spectrum data. As an example, the disease information may be information on whether a lesion tissue exists in the target from which the spectrum data is obtained. For example, the analysis device 200 may obtain spectrum data from the laser device 100 and perform diagnosis on the basis of the spectrum data.

The analysis device 200 may use techniques such as big data and artificial intelligence to perform the diagnosis. For example, the analysis device 200 may execute a machine-learned program to provide disease information on the specimen. A detailed description of examples in which diagnosis is performed by the analysis device 200 will be provided below.

The diagnostic system 10 described above may be provided as a physically single device or a plurality of devices. For example, the diagnostic system 10 may be provided as a single diagnostic device in which the laser device 100 and the analysis device 200 are physically integrated. That is, the diagnostic system 10 may be implemented as a physically single device. As another example, as the laser device 100 and the analysis device 200 are provided as physically separate devices, the diagnostic system 10 may be implemented as a system including a plurality of devices. That is, the diagnostic system 10 may be implemented as two devices of the laser device 100 and the analysis device 200.

Of course, it should be noted that the physical implementation of the diagnostic system 10 is not limited to the above-described examples.

In some embodiments, the diagnostic system 10 may be implemented in various forms.

According to one example, the diagnostic system 10 may be implemented in a stand-alone type. Here, the stand-alone type may refer to a type capable of independently performing a diagnostic method according to one embodiment of the present specification without additional external equipment.

According to another example, the diagnostic system 10 may be implemented in an add-on type. Here, the add-on type may refer to a type capable of performing the diagnostic method according to one embodiment of the present specification in cooperation with external equipment.

Hereinafter, the laser device 100 according to one embodiment of the present specification will be described.

Figure 2:
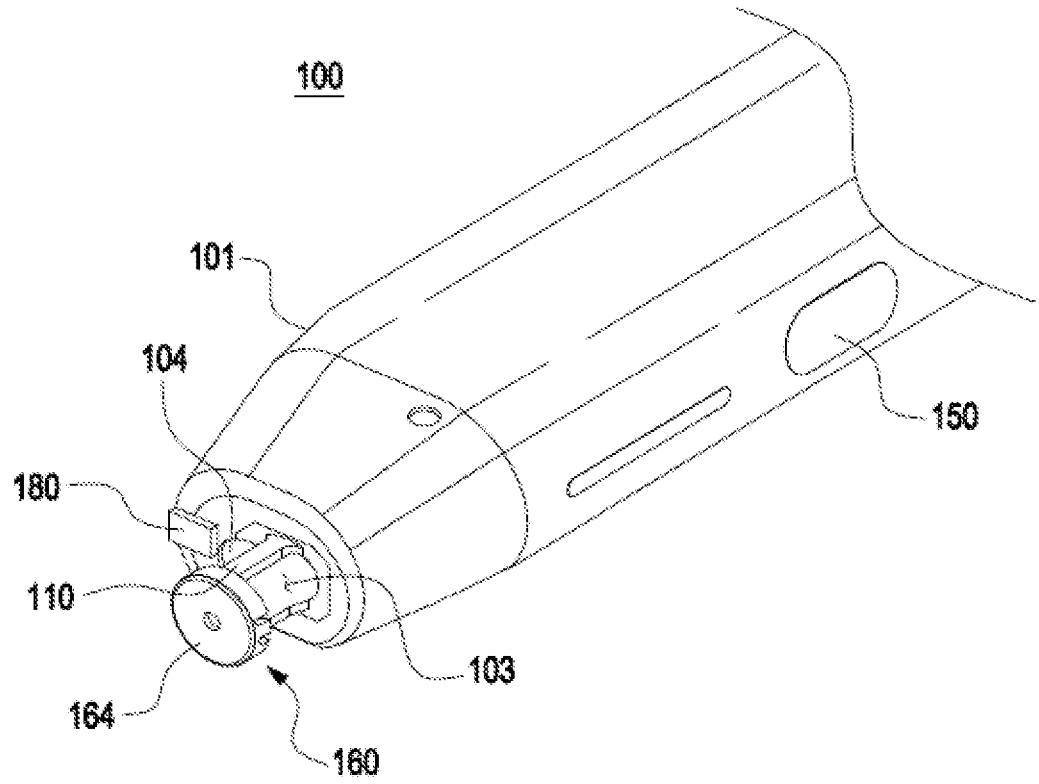
FIG. 2 is a perspective view of a laser device according to various embodiments.
Figure 3:
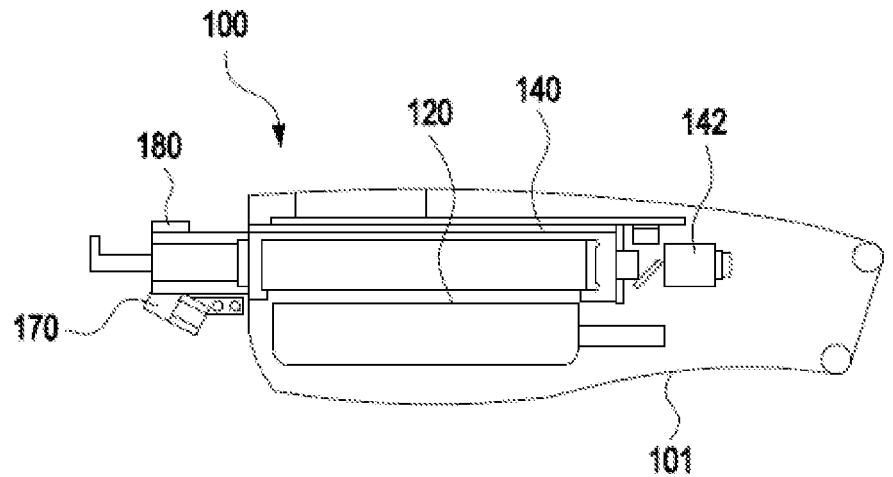
FIG. 3 is a perspective view of the laser device according to various embodiments.

FIGS. 2 and 3 illustrate implementation examples of the laser device according to various embodiments.

FIG. 2 is a perspective view of the laser device according to various embodiments. FIG. 3 is a perspective view of the laser device according to various embodiments.

Referring to FIGS. 2 and 3, the laser device 100 may include all or some of a housing 101, a laser activation unit 120, a guide module 142, a light collection module 170, and an imaging module 180.

According to various embodiments, the housing 101 may provide an outer shape of the laser device 100 and include an accommodation space for mounting components therein.

According to various embodiments, the laser activation unit 120 may be disposed inside the housing 101. In one embodiment, the laser activation unit 120 may output a pulsed beam. For example, the laser activation unit 120 may include a flash lamp and a laser-activating medium configured to receive energy from the flash lamp and oscillate a laser. The housing 101 may include an opening 103 so that the pulsed beam output from the laser activation unit 120 can be transmitted to the outside of the housing.

According to various embodiments, a circuit board 140 may be disposed inside the housing 101 and electrically connected to the laser activation unit 120 and the guide module 142. In one embodiment, the circuit board 140 may include an external power source or an internal power source (not shown) and supply necessary power to the laser activation unit 120 and the guide module 142. In addition, a processor (e.g., a first controller 1001 in FIG. 5) provided in the circuit board 140 may control overall operations of the laser activation unit 120, the guide module 142, and/or the imaging module 180.

According to various embodiments, the guide module 142 may output guide light. In one embodiment, the guide module 142 may be a laser diode that emits light in a visible light region. The guide module 142 may output the guide light in a direction corresponding to a traveling direction of the pulsed beam output from the laser activation unit 120. For example, in a state in which a guide tip 160 is in contact with the skin, a position at which the pulsed beam is applied may correspond to a position at which the guide beam is projected onto the specimen. Accordingly, the guide module 142 outputs the guide light to the outside through the opening 103, and a user can identify the guide light with the naked eye to determine a radiation position of the pulsed beam.

According to various embodiments, the laser device 100 may include the guide tip 160 provided in a periphery of the opening 103. In one embodiment, the guide tip 160 may extend from the housing 101 to come into contact with at least a part of the specimen. For example, the guide tip 160 may include a length unit 110 having a predetermined length so that a focal length of the pulsed beam output from the laser activation unit 120 corresponds to a moving distance (for example, a distance from the laser activation unit 120 to the specimen) of the pulsed beam.

According to various embodiments, a contact unit 164 may be disposed on one side of the length unit 110. The contact unit 164 may be in contact with the specimen. In some embodiments, the contact unit 164 may be formed of a transparent material and/or may include an opening such that the user of the laser device 100 can recognize the radiation position of the pulsed beam with the naked eye.

According to various embodiments, the housing 101 may include a switch 150. The switch 150 may receive an input of the user and induce an operation of the laser activation unit 120 and/or the guide module 142. In addition, as will be described below, the switch 150 may also induce an operation of the imaging module 180.

According to various embodiments, the laser device 100 may include the light collection module 170 and the imaging module 180.

According to various embodiments, the light collection module 170 may be provided near the opening 103 and/or the guide tip 160. In one embodiment, the light collection module 170 may collect light induced by radiating the specimen with the pulsed beam output from the laser activation unit 120. The light collection module 170 may be connected to the analysis device 200 through a separate optical member (e.g., an optical fiber) and may transmit the collected light to the analysis device 200. For example, the analysis device 200 may receive light and obtain spectrum data using a spectrometer (e.g., a spectrometer 2050 in FIG. 6).

In one embodiment, the light collection module 170 may be disposed to face the radiation position of the pulsed beam. For example, the light collection module 170 may be disposed to face at least a partial region of one end of the guide tip 160, which is a destination of the pulsed beam, in order to efficiently receive the light induced by the pulsed beam.

According to various embodiments, the imaging module 180 may be disposed in parallel to the light collection module 170 and/or near the light collection module 170. In one embodiment, the imaging module 180 may capture an image in a periphery of the guide tip 160. For example, the imaging module 180 may capture an image of a partial region of a specimen radiated with the guide beam. As will be described below, the user can clearly grasp the radiation position of the pulsed beam with reference to the image in which the guide beam is projected on the specimen.

Figure 4:
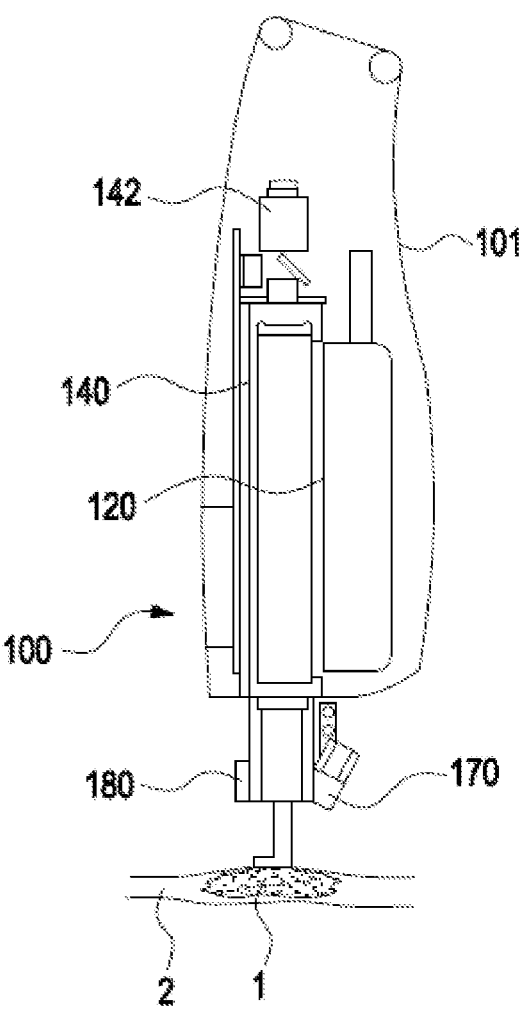
FIG. 4 is a view illustrating a usage aspect of the laser device according to various embodiments.

FIG. 4 is a view illustrating a usage aspect of the laser device according to various embodiments.

Referring to FIG. 4, the laser device 100 may radiate a pulsed beam to a normal tissue 1 and/or a suspicious tissue 2 and induce plasma ablation for obtaining spectrum data. The laser device 100 illustrated in FIG. 4 may mean the same configuration as the laser device 100 of FIGS. 2 and 3 in whole or in part.

In the following description, for convenience of description, the specimen will be described with a focus on a skin tissue of the user (or a patient). In addition, the specimen may be distinguished by physical properties of the skin tissue. For example, the specimen may be distinguished into the normal tissue 1 and the suspicious tissue 2.

In one embodiment, the normal tissue 1 may mean a skin tissue that is previously confirmed as having no lesion, or recognized as having no lesion when viewed with the naked eye. In addition, the suspicious tissue 2 may mean a tissue previously confirmed as having a lesion, or a tissue that is suspected of having a lesion when viewed with the naked eye and requires confirmation. In one embodiment, the suspicious tissue 2 may mean a tissue having a shape different from that of a surrounding skin tissue when viewed with the naked eye. For example, the suspicious tissue 2 may be a skin cancer tissue. Here, the skin cancer tissue may be, for example, melanoma. In addition, the suspicious tissue 2 may not be a lesion tissue, such as a nevus or benign tissue.

According to various embodiments, a system (e.g., the system 10 in FIG. 1) may determine whether the suspicious tissue 2 has a lesion on the basis of at least a part of spectrum data related to the normal tissue 1 and/or the suspicious tissue 2. In determining whether the suspicious tissue 2 has a lesion, a position at which the pulsed beam is radiated may be applied as an important consideration element. For example, since a spot size of the pulsed beam is very small as compared to a general size of the suspicious tissue 2, the disease information provided by the system 10 may vary according to the radiation position of the pulsed beam even in the case of the same suspicious tissue 2.

In the system 10 according to various embodiments, since the user visually confirms the radiation position of the pulsed beam through the imaging module 180, more accurate disease information (diagnosis result) for the suspicious tissue 2 can be provided by considering the analysis result of the spectrum data according to the radiation position of the pulsed beam.

Figure 5:
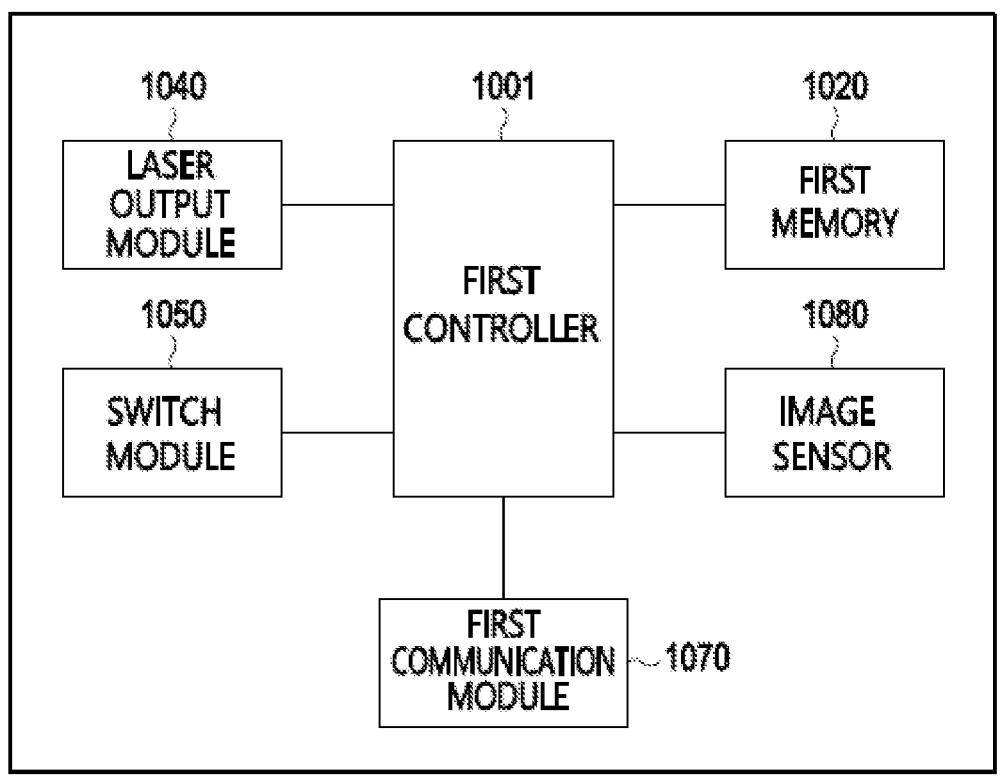
FIG. 5 is a block diagram illustrating an electrical configuration of the laser device according to various embodiments.

FIG. 5 is a block diagram illustrating an electrical configuration of the laser device according to various embodiments.

Referring to FIG. 5, the laser device 100 may include a laser output module 1040, a switch module 1050, a first controller 1001, a first memory 1020, and a first communication module 1070.

Hereinafter, each configuration of the laser device 100 according to one embodiment of the present specification will be described.

The laser output module 1040 may radiate a laser to a specimen. Alternatively, the laser output module 1040 may guide a laser output from external equipment to be radiated to the specimen. The laser output module 1040 may mean the same configuration as the laser activation unit 120 described above with reference to FIGS. 2 and 3 in whole or in part.

The laser output module 1040 may output a laser generated from an active laser medium 1212 in the form of a continuous beam or a pulsed beam. Here, when the pulsed laser is output, the laser generated from the active laser medium 1212 may be excited by a pulse signal, or Q-switching and mode synchronization may be used, and a pulse duration is adjusted such that an output intensity (energy per unit time) may be adjusted by the laser. In addition, the laser output module 1040 may output a laser having a specific wavelength. At this point, the wavelength of the output laser may be determined by a type of the active laser medium 1212. For example, when the active laser medium 1212 is provided as an Nd:YAG material, the laser output module 1040 may output a 1064 nm laser, a laser with a harmonic wavelength of a 1064 nm laser, or a laser in which a 1064 nm laser becomes a harmonic wavelength. In the following description, for convenience of description, the description will be focused on the laser output in the form of a pulsed beam.

A laser induced breakdown phenomenon may occur in a specimen to which the laser is radiated. Specifically, when the laser is radiated to the body tissue by the laser output module 1040, a part of the body tissue is ablated such that plasma may be formed. In order to generate the laser induced breakdown phenomenon as described above, characteristics such as a laser intensity, an emission area, and the like may need to satisfy certain conditions. To this end, the laser output module 1040 may adjust the characteristics of the laser radiated to the specimen. Here, the emission area may mean an area in which the laser radiated to the specimen is incident thereto.

The spectrometer 2050 may detect an intensity for each wavelength of input light. For example, the spectrometer 2050 may detect an intensity for each wavelength of light which is collected by receiving the light collected by the light collection module 170 through a light transmitting member.

The first communication module 1070 may perform communication with an external device. The laser device 100 may transmit and receive data to and from the analysis device 200 or an external server through the first communication module 1070.

The first communication module 1070 is broadly divided into a wired type module and a wireless type module. Since each of the wired type module and the wireless type module has an advantage and a disadvantage, in some cases, the wired type module and the wireless type module may be simultaneously provided in the laser device 100.

Here, in the case of the wired type module, a local area network (LAN) or a Universal Serial Bus (USB) communication is a typical example, and other methods are possible. In addition, in the case of the wireless type module, a wireless personal area network (WPAN)-based communication method such as Bluetooth or ZigBee may be mainly used. However, since a wireless communication protocol is not limited thereto, the wireless type communication module may use a wireless local area network (WLAN)-based communication method such as Wi-Fi or other known communication methods.

The first memory 1020 may store various pieces of information. Various pieces of data may be temporarily or semi-permanently stored in the first memory 1020. Examples of the first memory 1020 may include a hard disk drive (HDD), a solid state drive (SSD), a flash memory, a read-only memory (ROM), a random access memory (RAM), and the like. The first memory 1020 may be provided in the form embedded in the laser device 100 or in the detachable form.

Various pieces of data required for an operation of the laser device 100 in addition to an operating system (OS) for operating the laser device 100 or a program for operating each component of the laser device 100 may be stored in the first memory 1020. For example, electrical signals or spectrum data generated on the basis of an amount of light detected by the spectrometer 2050 may be stored in the first memory 1020.

The first controller 1001 may control an overall operation of the laser device 100.

The first controller 1001 may be implemented as a central processing unit (CPU) or a device similar to the CPU according to hardware, software, or a combination thereof. The first controller 1001 may be provided in the form of an electronic circuit for processing an electrical signal to perform a control function in hardware, and may be provided in the form of a program or code for driving a hardware circuit in software.

The laser device 100 may have a separate power supply unit or receive power from the outside in a wired or wireless manner, and may have a separate switch configured to control the power supply unit.

Hereinafter, the analysis device 200 according to one embodiment of the present specification will be described.

Figure 6:
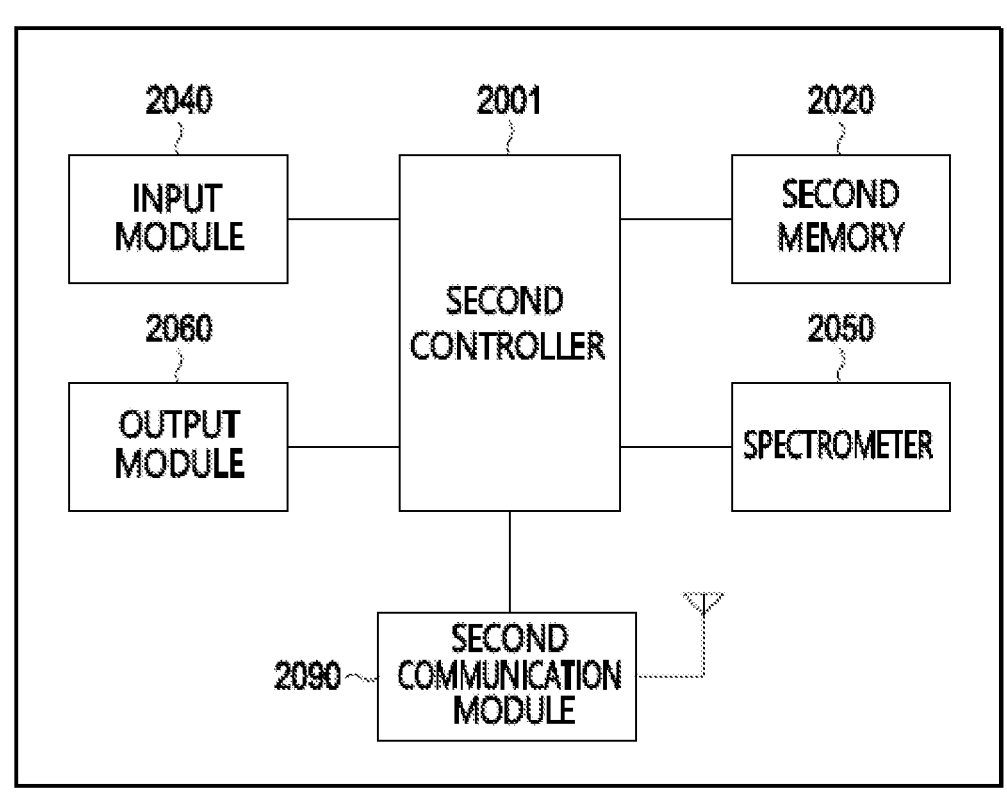
FIG. 6 is a block diagram illustrating an analysis device according to various embodiments.

FIG. 6 is a block diagram illustrating an analysis device according to various embodiments.

Referring to FIG. 6, the analysis device 200 may include a second controller 2001, an input module 2040, an output module 2060, a second communication module 2090, and a second memory 2020.

According to one embodiment of the present specification, the analysis device 200 may perform diagnosis on a specimen. In addition, the analysis device 200 may provide a user with a result of the diagnosis performed on the specimen.

The analysis device 200 may use various pieces of data in diagnosing the specimen. For example, the analysis device 200 may use at least one among spectrum data, image data, and sound data.

Here, the analysis device 200 may receive data for diagnosing the specimen from the laser device 100. The analysis device 200 may obtain spectrum data from the laser device 100 and use the spectrum data to perform diagnosis on the specimen. Specifically, for example, when the laser device 100 radiates a laser to the specimen to form plasma and provides the analysis device 200 with spectrum data obtained by spectroscopically analyzing plasma light from the plasma, the analysis device 200 may use the spectrum data to determine whether a disease is present in the specimen.

According to one embodiment of the present specification, the second controller 2001 may obtain the spectrum data for the specimen from the laser device 100 using the second communication module 2090, determine a state of the specimen, such as the presence of absence of a disease, a health status, a composition, and the like, using a diagnostic program stored in the second memory 2020, and output the determination result to the output module 2060, so that the analysis device 200 can perform diagnosis on the specimen.

The second communication module 2090 may perform communication with an external device. The analysis device 200 may perform data communication with the laser device 100 or an external server using the second communication module 2090. For example, the analysis device 200 may obtain data required for diagnosis on the specimen from the laser device 100 using the second communication module 2090.

The second communication module 2090 may be provided similar to the first communication module 1070, and thus a more detailed description thereof will be omitted.

The second memory 2020 may store various pieces of information of the analysis device 200.

Various pieces of data required for an operation of the analysis device 200 in addition to an OS for driving the analysis device 200 or a program for operating each configuration of the analysis device 200 may be stored in the second memory 2020. For example, a program for processing spectrum data about the specimen and an artificial neural network for data analysis may be stored in the second memory 2020.

The second memory 2020 may be provided similar to the first memory 1020, and thus a more detailed description thereof will be omitted.

The input module 2040 may receive a user input from a user. The user input may be made in various forms such as a key input, a touch input, and a voice input. The input module 2040 is a comprehensive concept including not only a keypad, a keyboard, and a mouse which have a traditional form as well as a touch sensor for detecting a touch of a user, but also various types of input parts for detecting or receiving various types of user inputs. In addition, the input module 2040 may be implemented in the form of an input interface (a USB port, a PS/2 port, and the like) for connecting an external input device for receiving a user input to an electronic device instead of a device for detecting the user input by itself.

The output module 2060 may output and provide various pieces of information to the user. The output module 2060 is a comprehensive concept including a display for outputting an image, a speaker for outputting a sound, a haptic device for generating vibrations, and various types of output devices. In addition to the above description, the output module 2060 may be implemented in the form of a port type output interface for connecting individual output devices to an electronic device.

The second controller 2001 may control an overall operation of the analysis device 200. For example, the second controller 2001 may generate a control signal so as to load a program for processing and analyzing data from the second memory 2020, process and analyze data obtained from the laser device 100, and provide the result to the user through the output module 2060.

The second controller 2001 may be provided similar to the first controller 1001, and thus a more detailed description thereof will be omitted.

The analysis device 200 may have a separate power supply unit or receive power from the outside in a wired or wireless manner and may have a separate switch for controlling the power supply unit.

Hereinafter, a diagnostic method according to one embodiment of the present specification will be described. In the following description, the diagnostic method according to one embodiment of the present specification is described as being performed by the above-described diagnostic system 10. However, since this is only for convenience of description, the diagnostic method according to one embodiment of the present specification is not limited to being performed by the above-described diagnostic system 10. That is, the diagnostic method, which will be described below, is not necessarily to be performed by only the above-described diagnostic system 10 and may be performed by another system or device having a function similar to that of the above-described diagnostic system 10.

Figure 7:
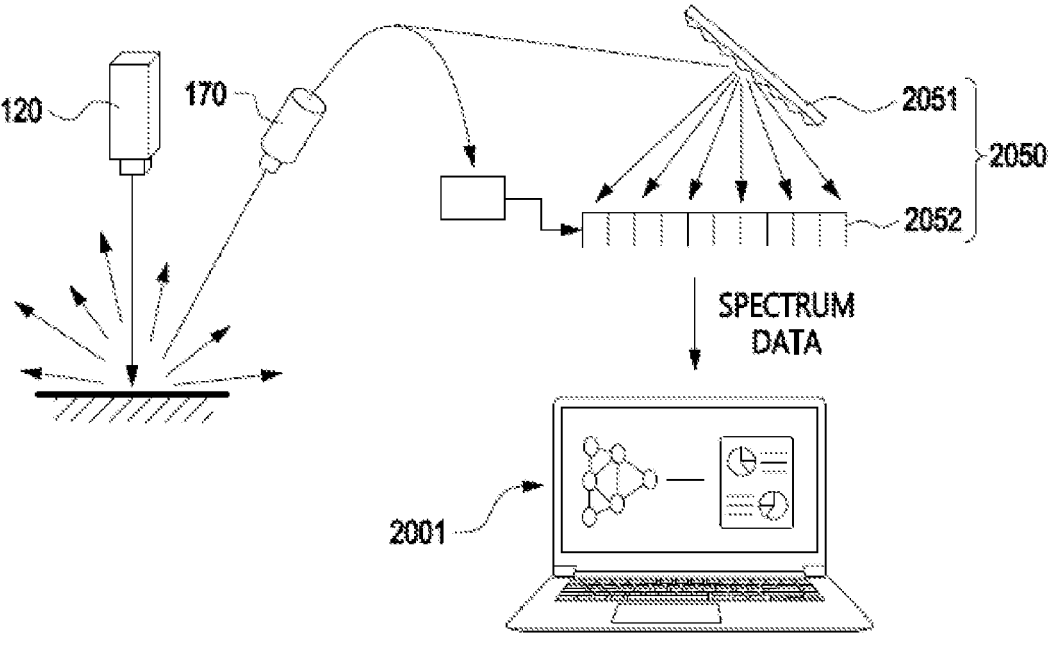
FIG. 7 is a view illustrating a schematic process of a disease information providing method according to various embodiments.

FIG. 7 is a view illustrating a schematic process of a disease information providing method according to various embodiments.

As shown in FIG. 7, the laser activation unit 120 of the laser device 100 may radiate a laser to a specimen. Here, the laser activation unit 120 may directly generate a laser to output the laser to the specimen or receive a laser from external equipment to output the laser to the specimen.

Plasma ablation is induced in the specimen to which the laser is radiated, and thus plasma may be formed in the specimen or in a periphery of the specimen. Here, the laser radiated to the specimen may include a pulsed laser having a predetermined intensity, a predetermined period, and a predetermined form so as to induce ablation in the specimen and form plasma. The intensity, period, and form of the laser radiated to the specimen may be set or adjusted by the laser activation unit 120.

The system 10 may collect light related to or caused due to the laser radiation from the specimen. Specifically, as shown in FIG. 7, the light collection module 170 of the laser device 100 may receive the light from the specimen.

For example, as shown in FIG. 7, when the laser is radiated to the specimen, light may be emitted in various directions, and the light collection module 170 may receive at least a part of the emitted light.

Here, the collected light may be provided to the spectrometer 2050 through the light transmitting member.

The system 10 may obtain spectrum data related to the collected light. Specifically, the laser device 100 or the spectrometer 2050 of the analysis device 200 may receive the collected light from the light collection module 170 and generate the spectrum data related to the collected light. A spectral member 2051 may receive the collected light from the light collection module 170 and spectroscopically divide the light according to a wavelength, and a sensor array 2052 may measure an intensity of the spectroscopically divided light for each wavelength.

The system 10 may perform diagnosis on the specimen using the obtained spectrum data. More specifically, the analysis device 200 may perform diagnosis using the spectrum data obtained by the laser device 100. For example, as shown in FIG. 7, the analysis device 200 may process the spectrum data and determine whether a disease is present in the specimen, a state of the specimen, or the like using a data analysis program or the like. In analyzing the spectrum data, the analysis device 200 may use a diagnostic algorithm utilizing an artificial neural network, machine learning or big data analysis, and the like. In addition, the analysis device 200 may provide a result of performing diagnosis on the specimen to the user through the output module 2060.

Hereinafter, the disease information providing method according to various embodiments will be described with reference to the drawings. In describing the flow of the disease information providing method illustrated in FIG. 8, FIGS. 9 to 12 may be referred together with FIG. 8. In addition, the above-described configurations or reference numerals may be referenced together.

Figure 8:
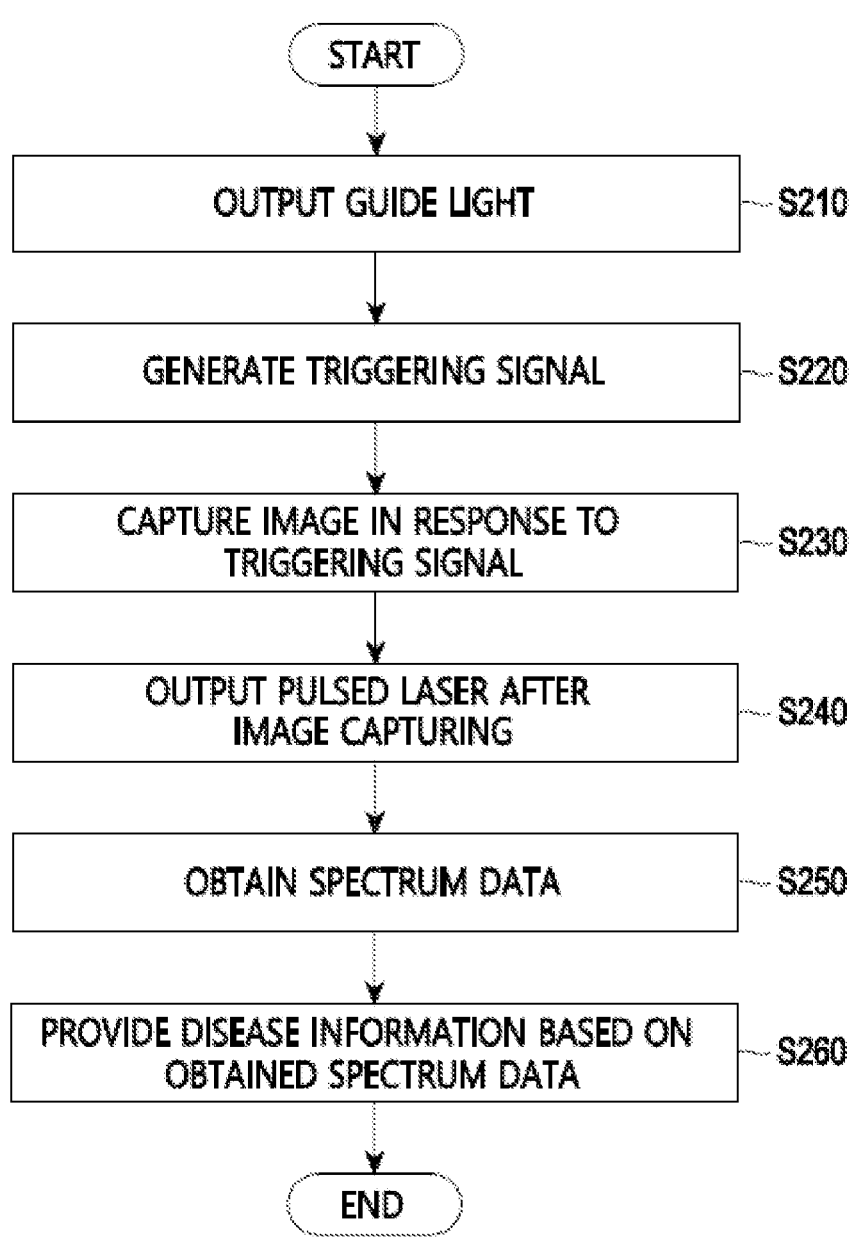
FIG. 8 is a flowchart of the disease information providing method according to various embodiments.
Figure 9:
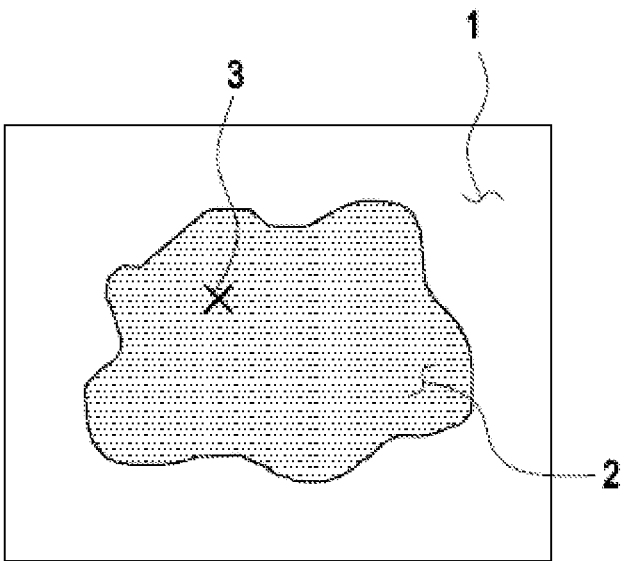
FIG. 9 is a view illustrating a situation in which guide light is radiated to a specimen, according to various embodiments.
Figure 10:
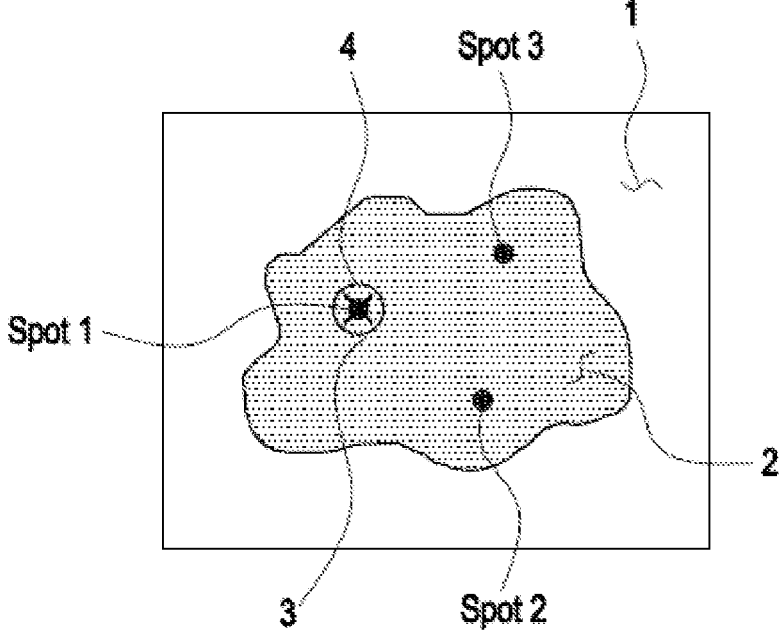
FIG. 10 is a view illustrating a case in which a plurality of pulsed beams are radiated, according to various embodiments.
Figure 11:
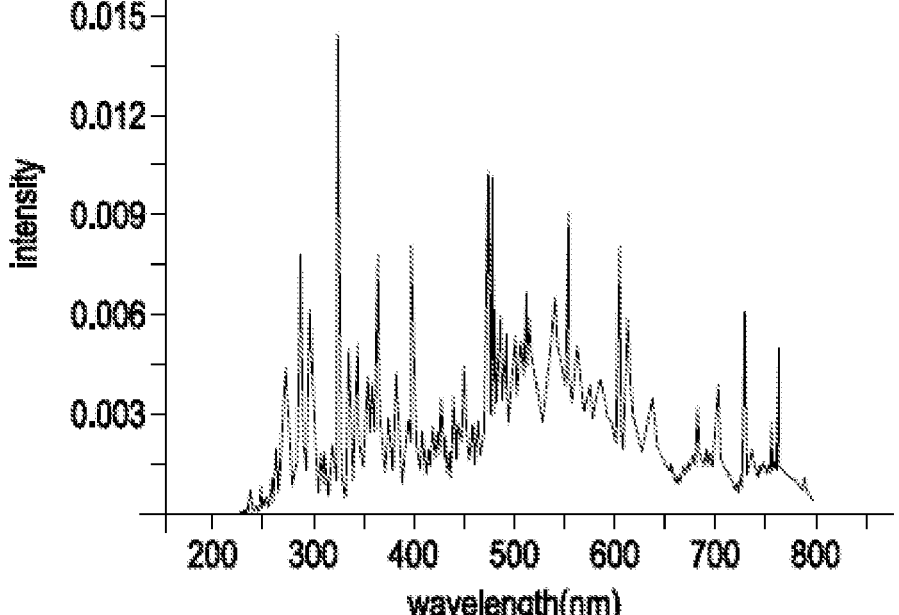
FIG. 11 illustrates one example of spectrum data according to various embodiments.
Figure 12:
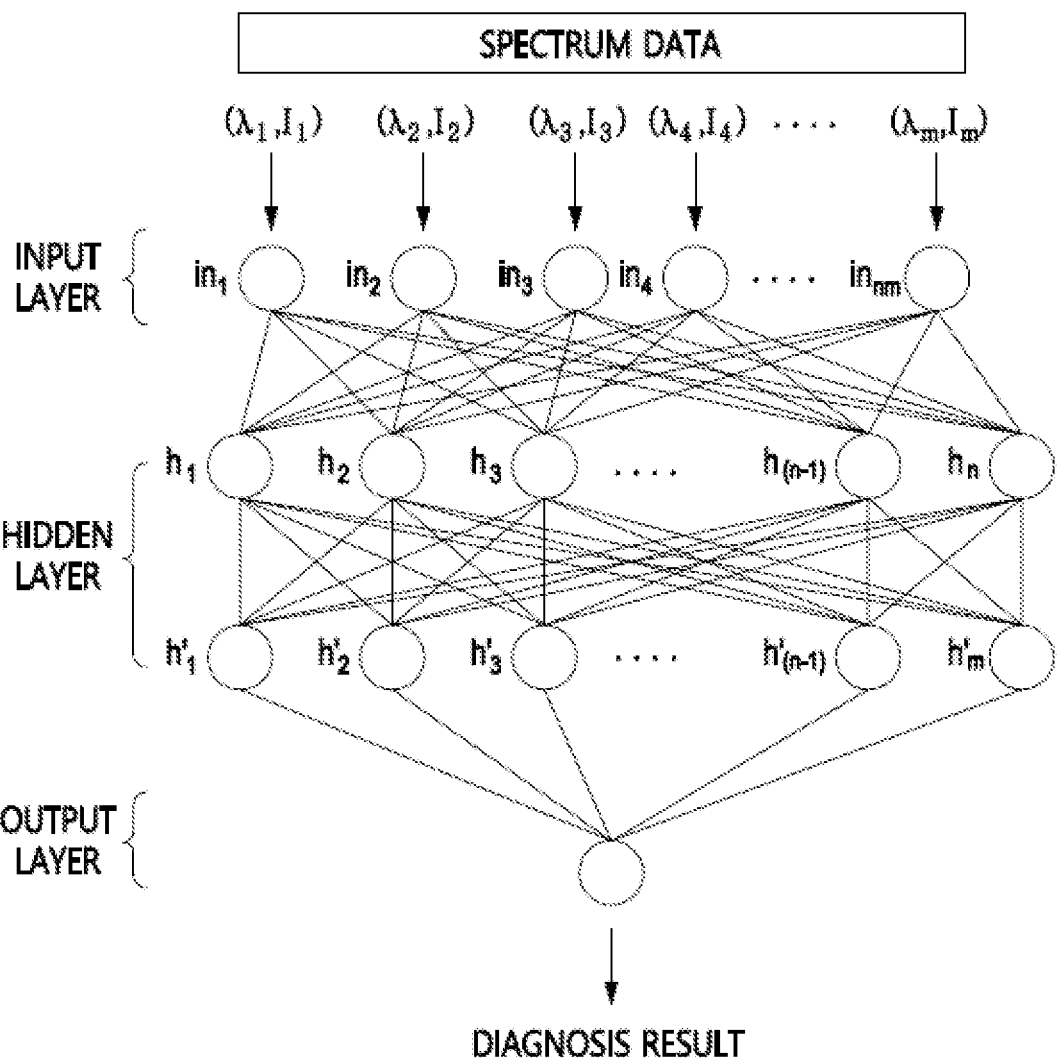
FIG. 12 illustrates one example of an artificial neural network according to various embodiments.

FIG. 8 is a flowchart illustrating the disease information providing method according to various embodiments. FIG. 9 is a view illustrating a situation in which guide light is radiated to a specimen, according to various embodiments. FIG. 10 is a view illustrating a case in which a plurality of pulsed beams are radiated, according to various embodiments. FIG. 11 illustrates one example of spectrum data according to various embodiments. FIG. 12 illustrates one example of an artificial neural network according to various embodiments.

Referring to FIG. 8, the disease information providing method performed in the system 10 may include outputting guide light (S210), generating a triggering signal (S220), capturing an image in response to the triggering signal (S230), outputting a pulsed beam after the capturing of the image (S240), obtaining spectrum data (S250), and providing disease information on the basis of the obtained spectrum data (S260).

According to various embodiments (particularly, referring to FIGS. 8 and 9), the system 10 may output guide light 3 (S210). In one embodiment, the laser device 100 may output the guide light 3 on a specimen, and a user may visually confirm the guide light 3 radiated on the specimen. For example, the laser device 100 may output the guide light 3 through the guide module 142 according to the operation of the user, and the user may confirm a position, at which the pulsed beam is to be radiated, while moving the guide light 3 on a normal tissue 1 or a suspicious tissue 2.

According to various embodiments, the system 10 may generate a triggering signal (S220. Here, the triggering signal may be generated in response to an input of the user. For example, when the user presses a switch (e.g., the switch 150 in FIG. 2), the first controller 1001 may generate a triggering signal for initiating an operation of the imaging module 180 and/or the laser activation unit 120.

According to various embodiments, the system 10 may capture an image of at least a partial region of the specimen, onto which the guide light 3 is being projected, in response to the triggering signal (S230). For example, the system 10 may capture an image of a partial region of the specimen and provide the captured image to the user through an output module (e.g., a display) provided in the analysis device 200. For example (referring to FIG. 9), the imaging module 180 may capture the image of the specimen such that the guide light 3 being projected onto the normal tissue 1 and/or the suspicious tissue 2 appears.

According to various embodiments, the system 10 may radiate the pulsed beam multiple times. In addition, the system 10 may capture images of at least some or all of positions at which the pulsed beam is radiated multiple times, and provide the images to the user through the output module 2060. For example (referring to FIG. 10), the system 10 may provide information on positions (hereinafter referred to as "laser radiation positions"), at which a plurality of lasers have been radiated, on the specimen (the normal tissue 1 or the suspicious tissue 2). Specifically, when the user is currently aiming the pulsed beam at a position to which the guide light 3 is radiated, the analysis device 200 may output information on a second laser radiation position spot 2 and a third laser radiation position spot 3, which are positions to which the pulsed beam is previously radiated together. When a target 4 to which the pulsed beam is radiated is designated at a position different from the position to which the pulsed beam was previously radiated, the user may aim the guide light 3 at a position different from the second laser radiation position spot 2 and the third laser radiation position spot 3 in consideration of the second laser radiation position spot 2 and the third laser radiation position spot 3 provided through the output module 2060.

For example, as shown in FIG. 10, the system 10 may provide the positions (e.g., the second laser radiation position spot 2 and/or the third laser radiation position spot 3) of the previously radiated pulsed beams as information related to guide light, whose images are respectively captured directly before the corresponding pulsed beams are radiated.

According to various embodiments, the system 10 may radiate the pulsed beam to the specimen in order to provide disease information (S240). In one embodiment, the radiation of the pulsed beam using the laser device 100 may be performed after image capturing. For example, in response to the triggering signal generated by the switch module 1050, the first controller 1001 may first capture an image of a partial region of the specimen to which the guide light is radiated, and then radiate the pulsed beam to the position at which the guide light is radiated, through the laser activation unit 120.

According to various embodiments, when the pulsed beam is radiated, the system 10 may obtain spectrum data related to the specimen (S250). In one embodiment, when the pulsed beam is radiated, plasma ablation occurs in at least a partial region (e.g., the position at which the guide light 3 is radiated) of the specimen, and the light collection module 170 of the laser device 100 may transmit light related to the plasma ablation to a spectrometer (e.g., the spectrometer 2050 in FIG. 6) of the analysis device 200. The spectrometer 2050 may spectroscopically divide the received light and obtain spectrum data.

Referring to FIGS. 9 and 10, the system 10 may obtain disease information corresponding to a spot, to which the pulsed beam is radiated, onto a suspicious tissue.

According to various embodiments, the pulsed beam may be radiated onto a plurality of spots Spot 1, Spot 2, and Spot 3 on the suspicious tissue. Plasma ablation may be induced in each of the plurality of spots Spot 1, Spot 2, and Spot 3. Accordingly, as will be described below, different pieces of disease information may be obtained from each of the plurality of spots Spot 1, Spot 2, and Spot 3. That is, even in the same suspicious tissue 2, different pieces of disease information may be obtained according to the radiation position of the pulsed beam. For example, even when the suspicious tissue 2 is a skin cancer tissue, a diagnosis result related to the skin cancer may not be obtained at a point corresponding to a first spot Spot 1. On the other hand, the diagnosis result related to the skin cancer may be obtained at points corresponding to a second spot Spot 2 or a third spot Spot 3. Consequently, the system 10 can provide more accurate disease information related to the suspicious tissue 2 by aggregating pieces of disease information obtained from the plurality of spots Spot 1, Spot 2, and Spot 3 in the same suspicious tissue 2.

According to various embodiments, the system 10 may capture an image of the guide light 3 so that the user can accurately recognize the radiation positions (radiation spots Spot 1, Spot 2, and Spot 3) of the pulsed beam. Here, the radiation positions of the guide light 3 are preferably substantially the same positions as the radiation spots Spot 1, Spot 2, and Spot 3 of the pulsed beam, but the present application is not limited thereto. As will be described below, the user may radiate the pulsed beam to the second spot Spot 2 different from the first spot Spot 1 in consideration of the position at which the image of the guide light 3 is captured. In the above and following description of the present disclosure, the terms "spot" and "target" may be used interchangeably.

Referring to FIG. 11, spectrum data according to various embodiments may include non-specific emission (continuous emission) having a continuous spectrum and element specific emission having a spectrum of a specific wavelength range. For example, the spectrometer 2050 according to one embodiment may be of a non-gated type in which a gating time thereof is set to a predetermined time or a separate gating time is not set, so that information related to both the continuous emission, which is predominantly observed immediately after the plasma ablation has occurred (i.e., immediately after the pulsed beam is radiated), and the element specific emission, which is generally more predominantly observed after the continuous emission, can be obtained. For example, a start time point of the gating time of the spectrometer 2050 according to one embodiment may be determined as one of time points in a period between a time point of the pulsed beam radiation and 10 ns, and an end time point of the gating time may be determined as a time point of about 10 µs after the pulsed beam radiation.

Meanwhile, when only the spectrum of the plasma emission (i.e., the non-specific emission) needs to be observed as necessary, a start time point of a plasma observation period may be set to a start time point of a second period, and an end time point of the plasma observation period may be set to a time point before an amount of the element specific emission becomes a predetermined level or more. That is, for example, the end time point of the plasma observation period may be set to a time point of about 1 μs after the laser is radiated to the specimen.

According to various embodiments, the system 10 may provide disease information on the basis of the obtained spectrum data (S260). In one embodiment, the analysis device 200 may provide disease information on the basis of the spectrum data obtained by using an artificial neural network, as will be described below. For example, the system 10 may use the obtained spectrum data as input data of the artificial neural network. Alternatively, the system 10 may process the obtained spectrum data into input data corresponding to the artificial neural network stored in the second memory 2020 and use the input data.

An artificial neural network used in various embodiments will be briefly described with reference to FIG. 12.

As described above, the system 10 may use various disease information providing algorithms to provide disease information.

For example, the disease information providing algorithm may be provided as an artificial neural network. Detailed examples of the artificial neural networks include a regression analysis artificial neural network (convolution neural network), a recurrent neural network, a deep neural network, and the like, and in the following description, the artificial neural network should be interpreted in a comprehensive meaning including all of the above-described artificial neural networks, various other artificial neural networks, and an artificial neural network in combination thereof.

Further, in addition to the above-described artificial neural network model, the disease information providing algorithm of the present disclosure may include a nearest neighbor algorithm (KNN), a random forest, a support vector machine (SVM), a principal component analysis (PCA), and the like, and may include an ensemble form of the above-described techniques or a form in which the above-described techniques are combined in various manners.

Furthermore, the disease information providing algorithm in the present specification is not necessarily limited to a machine learning model. That is, the diagnostic algorithm may include various determination/decision algorithms rather than the machine learning model.

In the present specification, a deep learning-based artificial neural network may be implemented logically or physically. That is, the artificial neural network may be implemented in hardware, software, or a combination thereof.

For example, the artificial neural network may be implemented as a program using an application such as Tensor-Flow of Google and the like. Here, the artificial neural network in the form of a program is provided with logically implemented layers, nodes, and lines connecting the logically implemented layers to the nodes and may be implemented by processing data through operations of a CPU or a graphics processing unit (GPU). In the present specification, the artificial neural network may be implemented through the second controller 2001 and the second memory 2020 of the analysis device 200. At this point, the second memory 2020 may store a weight value of each node constituting the artificial neural network, a connection relationship between the nodes, a configuration of the node, and the like, and the second controller 2001 may input spectrum data to an input layer, and then, may calculate a node value at each node and calculate a result value at an output layer.

As another example, the artificial neural network may be provided as hardware such as a neuromorphic chip implemented with various electrical circuits including an application specific integrated circuit (ASIC) form or a field programmable gate array (FPGA) form for dedicatedly processing the artificial neural network.

Hereinafter, a description will be given with reference to FIGS. 13 and 14.

FIG. 13 is a flowchart of a disease information providing method according to another embodiment. FIG. 14 is a view illustrating a process of implementing the disease information providing method of FIG. 13.

Figure 14:
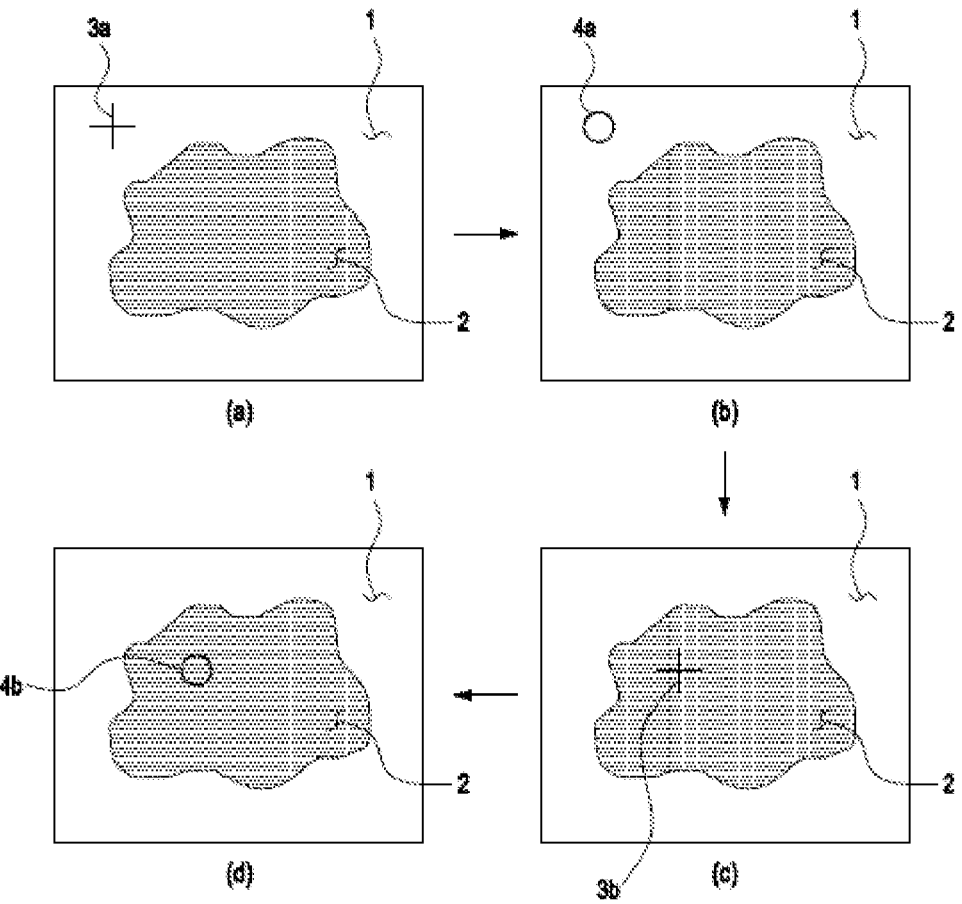
FIG. 14 is a view illustrating a process of implementing the disease information providing method of FIG. 13.

Referring to FIGS. 13 and 14, the system 10 may provide disease information on the basis of spectrum data obtained from at least two different positions.

First, referring to FIG. 13, the disease information providing method may include outputting first guide light (S310), generating a first triggering signal (S312), capturing a first image (S314), outputting a first pulsed beam (S316), obtaining reference spectrum data on the basis of the first pulsed beam (S318), outputting second guide light (S320), generating a second triggering signal (S322), capturing a second image (S324), outputting a second pulsed beam (S326), obtaining target spectrum data on the basis of the second pulsed beam (S328), and providing disease information on the basis of the reference spectrum data and the target spectrum data (S330).

Unless otherwise specified, the descriptions of operation S210 to operation S250 of FIG. 8 may be equally applied to operation of outputting the first guide light (S310) to operation of obtaining the reference spectrum data (S318), and thus repeated descriptions will be omitted.

According to various embodiments, the system 10 may project first guide light 3a onto a normal tissue 1 (S310). Thereafter, in response to a user input, the system 10 may generate a first triggering signal (S312), and capture a first image, which is obtained by capturing at least a partial region of a specimen (the normal tissue 1 and/or the suspicious tissue 2) such that the first guide light 3a is included, in response to the first triggering signal (S314). After capturing the first image, the system 10 may output a first pulsed beam to a position at which the first guide light 3a is being projected (S316). The system 10 may obtain reference spectrum data, which is related onto the normal tissue 1, at a first target 4a which is the position at which the first pulsed beam is radiated (S318).

According to various embodiments, the system 10 may project second guide light 3b onto the suspicious tissue 2 (S320). In one embodiment, as will be described below, the system 10 may obtain disease information on the basis of spectrum data obtained from the normal tissue 1 and spectrum data obtained from the suspicious tissue 2, and thus, the system 10 may project the second guide light 3b to a position different from the first target 4a on the suspicious tissue 2. In some embodiments, the system 10 may provide the user with an image, in which the first guide light 3a is captured, through the output module 2060, and the user may adjust the position of the second guide light 3b to be located at a position different from the position of the first guide light 3a.

According to various embodiments, while the second guide light 3b is being projected, the system 10 may generate a second triggering signal in response to a user input (S322).

According to various embodiments, when the second triggering signal is generated, the system 10 may capture a second image in response to the second triggering signal (S324). For example, the second image may mean an image in which at least a partial region of the specimen (the normal tissue 1 and/or the suspicious tissue 2) is captured such that the second guide light 3b appears. In some embodiments, the first image and the second image may be captured in a composition corresponding to each other. The user may receive accurate disease information at the position, to which the pulsed beam is radiated, by comparing the first image and the second image captured at the composition corresponding to each other.

According to various embodiments, after capturing the second image, the system 10 may output a second pulsed beam (S326). For example, the system 10 may output the second pulsed beam to the position to which the second guide light 3b is output.

According to various embodiments, the system 10 may obtain target spectrum data related to a second target 4b which is a position to which the second pulsed beam is output (S328). For example, the target spectrum data may mean spectrum data related to the suspicious tissue 2. Alternatively, the target spectrum data may mean spectrum data at a position in which disease information is required to be provided.

According to various embodiments, the system 10 may provide disease information on the basis of the reference spectrum data and the target spectrum data (S330). For example, the analysis device 200 may provide disease information related to the second target 4b using an artificial neural network stored in the second memory 2020. Here, input data of the artificial neural network may be obtained by combining the reference spectrum data and the target spectrum data. In obtaining the disease information on the second target 4b, the accuracy of the disease information may be improved by further using the reference spectrum data related to the normal tissue 1 in addition to the target spectrum data. To this end, the artificial neural network may be trained using training data in which the reference spectrum data and the target spectrum data are combined.

According to various embodiments, the artificial neural network may use pieces of reference spectrum data and/or target spectrum data in order to provide more accurate disease information.

Figure 15:
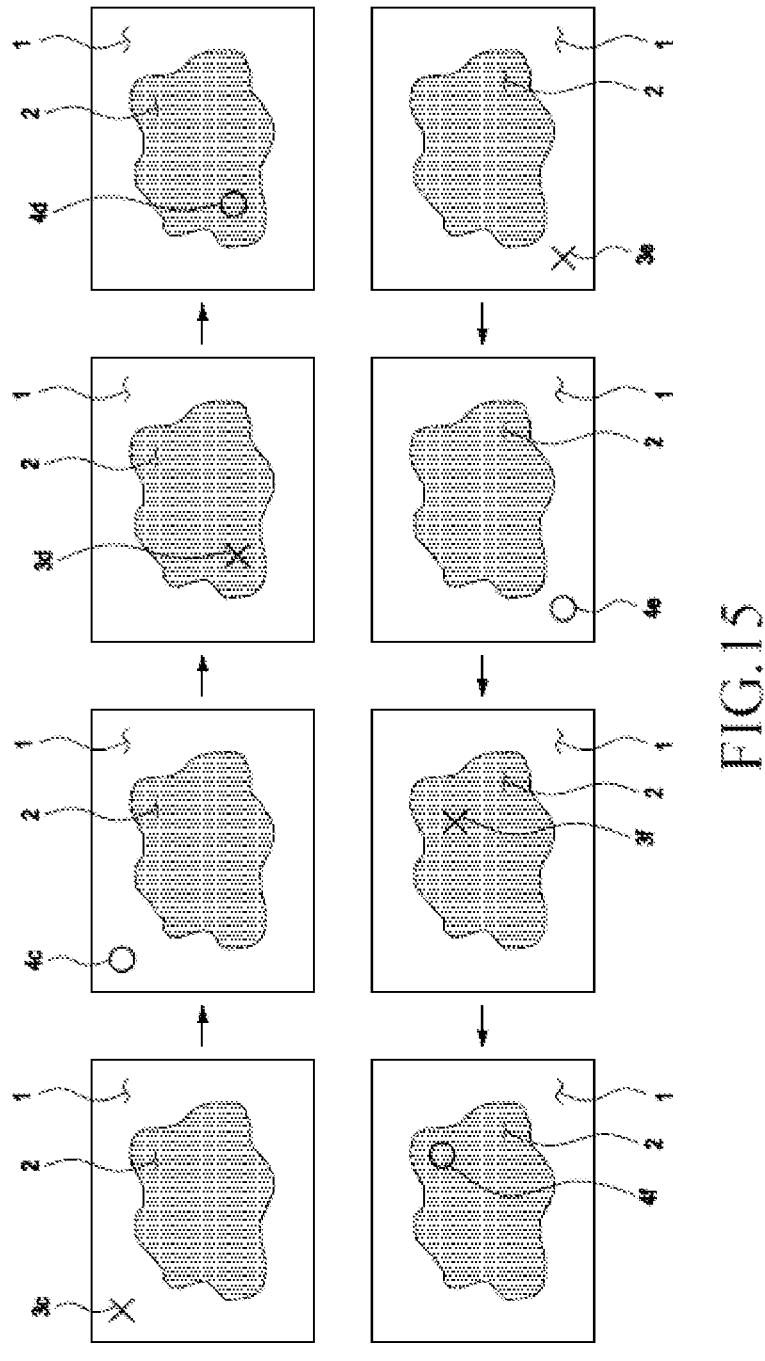
FIG. 15 is a view illustrating an application of the disease information providing method of FIG. 13.

FIG. 15 is a view illustrating an application of the disease information providing method of FIG. 13.

Referring to FIG. 15, the system 10 may provide disease information using a plurality of pieces of reference spectrum data and a plurality of pieces of target spectrum data.

According to various embodiments, the system 10 may obtain first reference spectrum data related to a first reference target 4c located in the normal tissue 1. As described above, a first image for first reference guide light 3c may be captured before a first pulsed beam for obtaining the first reference target spectrum data is radiated.

According to various embodiments, the system 10 may obtain first target spectrum data related to the suspicious tissue 2 in order to compare the first target spectrum data with the first reference spectrum data. For example, the system 10 may obtain first target spectrum data on a first target 4d located at a position different from that of the first reference target 4c on the suspicious tissue 2. Here, before obtaining the spectrum data on the first target 4d, the system 10 may capture a second image of first target guide light 3d pointing at the first target 4d.

According to various embodiments, the system 10 may obtain second reference spectrum data different from the first reference spectrum data. In one embodiment, the system 10 may obtain second reference spectrum data related to a second reference target 4e that is located in the normal tissue 1 and is different from the first reference target 4c. Here, the system 10 may provide the user with the first image in which the first reference guide light 3c, which is a basis of the first reference spectrum data, is captured, through the output module 2060, and the user may aim second reference guide light 3e at a position different from the first reference target 4c with reference to the first image. In some embodiments, the system 10 may capture a third image in which the second reference guide light 3e is captured, before obtaining the second reference spectrum data. The third image may be used when more reference spectrum data is needed in the normal tissue 1.

According to various embodiments, the system 10 may obtain second target spectrum data for comparison with the second reference spectrum data and/or the first reference spectrum data. The second target spectrum data may be spectrum data related to a second target 4f that exists at a position different from that of the first target 4d in the suspicious tissue 2. Before obtaining the second target spectrum data, the system 10 may obtain a fourth image including second target guide light 3f. The fourth image may be used when additional disease information is required at a position different from the first target 4d and/or the second target 4f in the suspicious tissue 2. According to one embodiment, the system 10 may provide disease information in the second target 4f by comparing the second reference spectrum data with the second target spectrum data. In addition, in providing the disease information in the second target 4f, the system 10 may further use the first reference spectrum data. In addition, in order to provide disease information in the first target 4d, the system 10 may use both the second reference spectrum data and the first reference spectrum data.

Figure 16:
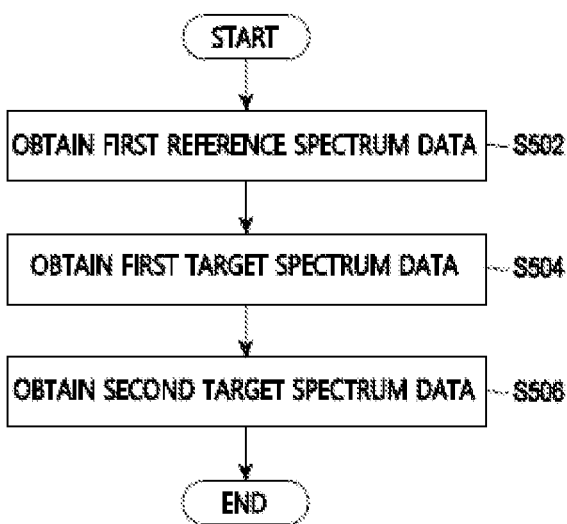
FIG. 16 illustrates a spectrum data obtaining method according to various embodiments.
Figure 17:
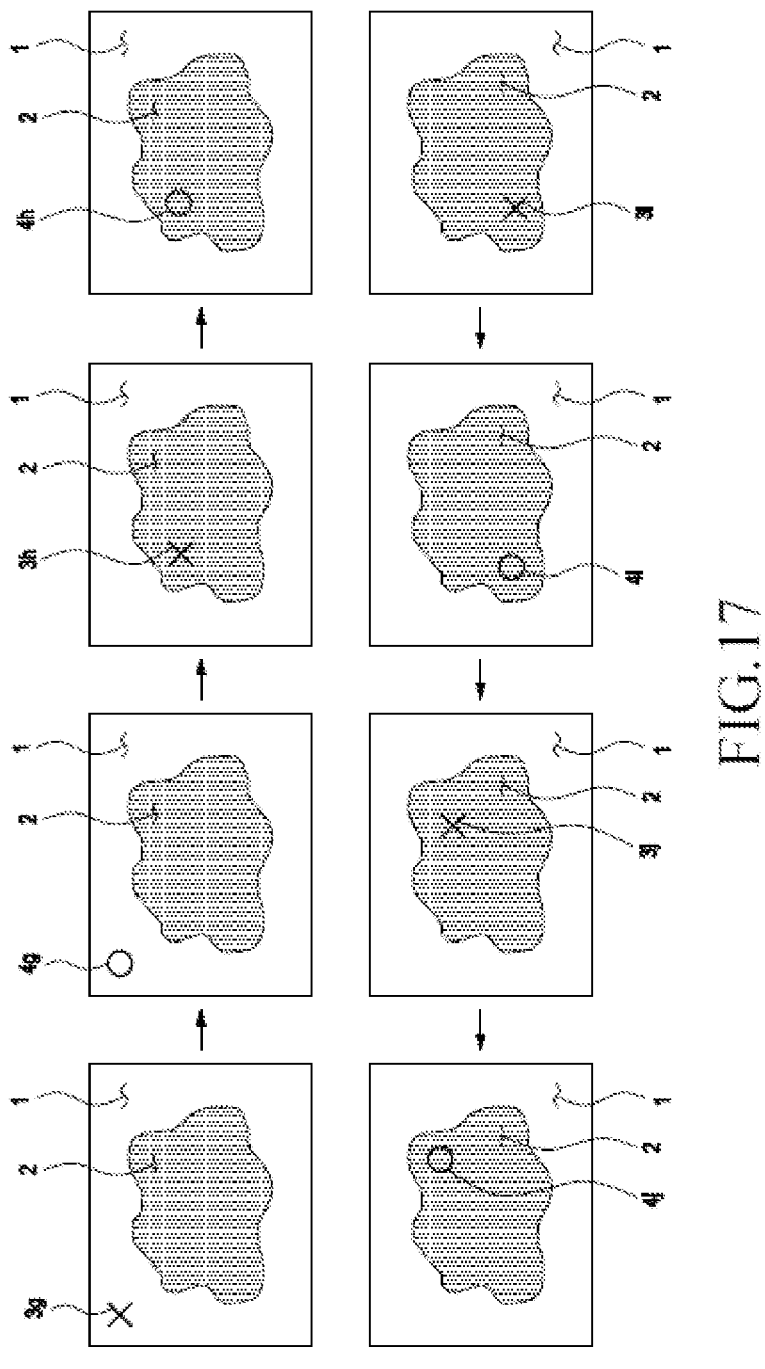
FIG. 17 is a view illustrating an implementation example of the spectrum data obtaining method of FIG. 16.

FIG. 16 illustrates a spectrum data obtaining method according to various embodiments. FIG. 17 is a view illustrating an implementation example of the spectrum data obtaining method of FIG. 16.

Referring to FIGS. 16 and 17, the spectrum data obtaining method according to various embodiments may include obtaining first reference spectrum data (S502), obtaining first target spectrum data (S504), and obtaining second target spectrum data (S506).

In each operation in FIG. 16, some of the method of FIG. 8 or the entire method of FIG. 8 may be equally or similarly applied to the obtaining of the spectrum data, and thus repeated descriptions will be omitted.

According to various embodiments, the system 10 may provide disease information on a plurality of targets on the basis of one reference spectrum data and a plurality of pieces of target spectrum data. For example, the system 10 may provide disease information on each of a plurality of targets 4h, 4i, and 4j on the basis of first reference spectrum data related to a first reference target 4g located in the normal tissue 1 and a plurality of pieces of target spectrum data respectively for the plurality of targets 4h,4i, and 4j located in the suspicious tissue 2.

According to various embodiments, the system 10 may obtain the first reference spectrum data for a first target 4g located in the normal tissue 1. Before obtaining the first reference spectrum data, a first image in which first reference guide light 3g is captured may be obtained. The first image may be used when additional reference spectrum data is needed, as described above.

According to various embodiments, the system 10 may obtain a plurality of different pieces of target spectrum data in the same suspicious tissue 2. In one embodiment, the system 10 may obtain second to fourth target spectrum data related to second to fourth targets 4h, 4i, and 4j. In obtaining the second to fourth target spectrum data, the system 10 may use all of second to fourth images, in which second to fourth target guide lights 3h, 3i, and 3j are respectively captured, and/or all or a part of the first image related to the reference spectrum data. For example, the user may obtain the second target spectrum data by aiming (outputting the second guide light 3*h* and the pulsed beam) at the second target 4*h* in the suspicious tissue 2 with reference to the first image in which the first reference guide light 3*g* is captured. Thereafter, with reference to the second image in which the second target guide light 3*h* is captured, the third target guide light 3*i* may be aimed at a position different from the second target guide light 3*h* in the same suspicious tissue 2, and the third target spectrum data for the third target 4*i* may be obtained. Similarly, the user may obtain the fourth target spectrum data on the fourth target 4*j*, which is different from the second target 4*h* and/or the third target 4*i*, in the same suspicious tissue 2 with reference to the second image and/or the third image in which the second guide light 3*h* and/or the third guide light 3*i* are captured.

According to various embodiments, the system 10 may provide disease information on each of the second to fourth targets 4*h*, 4*i*, and 4*j* by comparing the first reference spectrum data with each of the second to fourth target spectrum data. In addition, the system 10 may provide the disease information on each of the second target 4*h* to the fourth target 4*j* with reference to at least some of the second to fourth target spectrum data and the first reference spectrum data. For example, the system 10 may also calculate the disease information on the second target 4*h* on the basis of the first reference spectrum data, the second target spectrum data, and the third target spectrum data.

Figure 18:
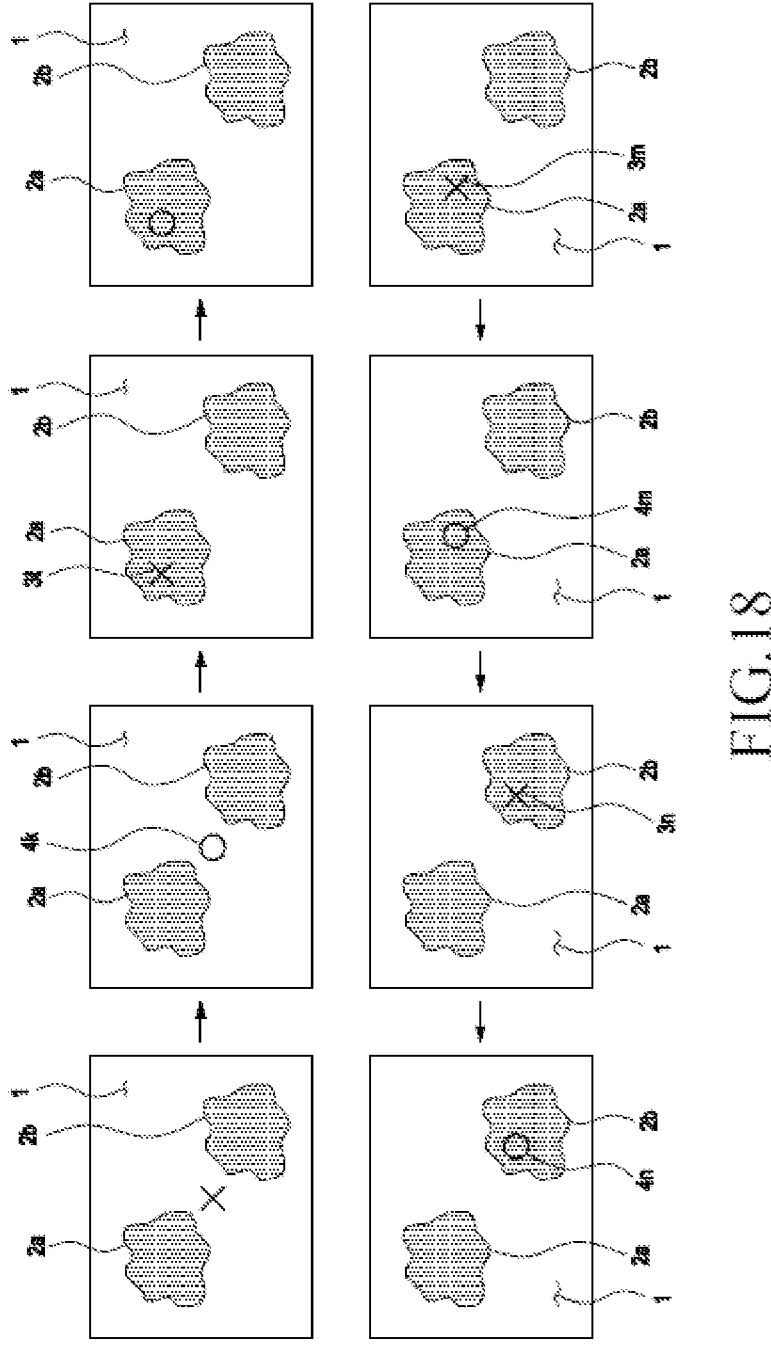
FIG. 18 is a view illustrating an application of the disease information providing method according to various embodiments.

FIG. 18 is a view illustrating an application of the disease information providing method according to various embodiments.

Referring to FIG. 18, the system 10 may use common reference spectrum data to identify disease information on each of two or more adjacent suspicious tissues 2*a* and 2*b*. Hereinafter, a position at which the common reference spectrum data is obtained is referred to as a "common target."

In describing FIG. 18, the descriptions given above with reference to FIGS. 8 and 15 to 17 may be referred to.

According to various embodiments, in identifying the disease information on each of the two or more suspicious tissues 2*a* and 2*b*, the system 10 may obtain the common reference spectrum data that can be applied to all the suspicious tissues 2*a* and 2*b*. In one embodiment, the common reference spectrum data may be obtained from at least a part of the normal tissue 1 between a first suspicious tissue 2*a* and a second suspicious tissue 2*b*. For example, a first common target 4*k* may be an intermediate point of the first suspicious tissue 2*a* and the second suspicious tissue 2*b*. As another example, the first common target 4*k* may be selected in the same body part as the first suspicious tissue 2*a* and the second suspicious tissue 2*b*. Here, the body part may be a hand, a foot, an arm, a back, a leg, a chest, or an abdomen. However, this is merely an example, and various embodiment modifications are possible.

In general, the prediction performance of the artificial neural network can be improved as training is performed with pieces of training data (e.g., generated by combining the reference spectrum data and the target spectrum data) having a characteristic of a consistent difference value between the normal tissue 1 and the suspicious tissue 2. Accordingly, it is desirable to obtain the reference spectrum data from a normal tissue (or a pigmented tissue) having a consistent difference in spectral characteristic with a skin cancer tissue.

For example, as the normal tissue (or the pigmented tissue) is located to be closer to the skin cancer tissue, probability that properties (e.g., a moisture content, hardness, ultraviolet ray exposure, a skin color, and the like) of the skin cancer tissue and the normal tissue (or the pigmented tissue) according to a general environment are commonly included in the spectrum data may be increased. Thus, the reference target for obtaining the reference spectrum data may be located within a predetermined distance from the suspicious tissue 2.

According to various embodiments, the system 10 may obtain first target spectrum data from a first target 4*l* located in the first suspicious tissue 2*a*. Before obtaining the first target spectrum data, the system 10 may obtain a first image in which first guide light 3*l*, which is a basis of the first target 4*l*, is captured.

According to various embodiments, the system 10 may obtain second target spectrum data related to a second target 4*m* different from the first target 4*l* in the first suspicious tissue 2*a*. For example, the user may project the second guide light 3*m* or radiate the pulsed beam to the second target 4*m* at a position different from the first target 4*l* in the first suspicious tissue 2*a* with reference to the first image in which the first guide light 3*l* is reflected.

According to various embodiments, the system 10 may obtain third target spectrum data from a third target 4*n* located in the second suspicious tissue 2*b*. Before obtaining the third target spectrum data, the system 10 may obtain a third image in which third guide light 3*n*, which is a basis of the third target spectrum data, is captured. For example, the user may project the third guide light 3*n* or radiate the pulsed beam to the second suspicious tissue 2*b* different from the first suspicious tissue 2*a* in which the first target 4*l* and the second target 4*m* are located with reference to the first image and/or the second image in which the first guide light 3*l* and/or the second guide light 3*m* are captured.

According to various embodiments, the system 10 may provide disease information on each of the first to third targets 4*l*, 4*m*, and 4*n* on the basis of the common reference spectrum data. For example, the analysis device 200 may obtain the disease information on each of the first to third targets 4*l*, 4*m*, and 4*n* by comparing the common reference spectrum data with each of the first to third target spectrum data. In addition, the analysis device 200 may also obtain the disease information on each of the first to third targets 4*l*, 4*m*, and 4*n* on the basis of at least some of the first to third target spectrum data and the common reference spectrum data. For example, the analysis device 200 may obtain the disease information on the third target 4*n* using all of the common reference spectrum data, the first target spectrum data, the second target spectrum data, and the third target spectrum data.

By obtaining the common reference spectrum data obtained in the normal tissue 1 between adjacent suspicious tissues 2*a* and 2*b*, the number of times of radiating the pulsed beam for obtaining reference spectrum data can be reduced.

Figure 19:
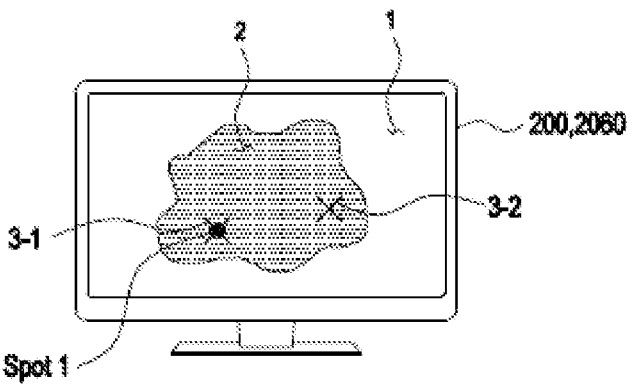
FIG. 19 illustrates one implementation example of an output module according to various embodiments.

FIG. 19 illustrates one implementation example of the output module according to various embodiments.

Referring to FIG. 19, the system 10 may guide a radiation position of a pulsed beam to a user through the output module 2060. The embodiment described in FIG. 19 may be applied, in part or in whole, to all the above-described embodiments.

According to various embodiments, the analysis device 200 may output images, in which pieces of guide light 3-1 and 3-2 are captured, through the output module 2060. In one embodiment, the analysis device 200 may output images in which a plurality of pieces of guide light 3-1 and 3-2 are reflected. For example, first guide light 3-1 may mean guide light that was previously projected, and second guide light 3-2 may mean guide light currently output. The user may aim the second guide light 3-2 at a position different from that of the first guide light 3-1 with reference to the first guide light 3-1 corresponding to a position spot 1 to which the pulsed beam was radiated in the past.

In some embodiments, the analysis device 200 may output an image in which the second guide light 3-2 is being captured in real time. At this time, the image of the first guide light 3-1, which was output in the past, may be overlaid on the image currently output, and the user may radiate the second guide light 3-2 to a position different from that of the first guide light 3-1. For example, the user may move the position of the second guide light 3-2 on the normal tissue 1 and/or the suspicious tissue 2.

Figure 20A:
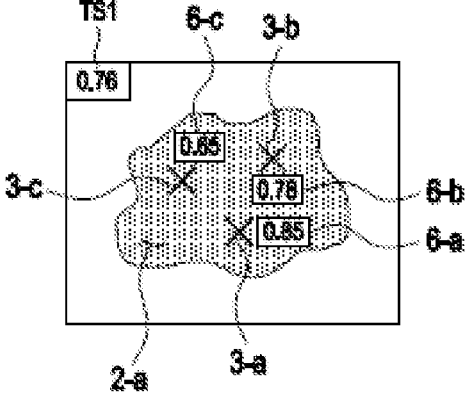
FIGS. 20A and 20B are views illustrating examples of proving disease information according to various embodiments.
Figure 20B:
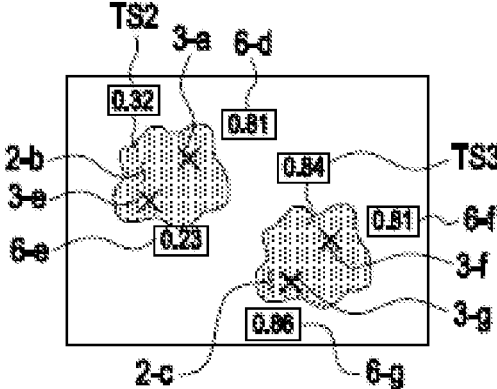

FIG. 20 is a view illustrating examples of proving disease information according to various embodiments.

Referring to FIG. 20, the system 10 may provide disease information on the suspicious tissue 2. All contents of the above-described embodiments may be combined with contents described in FIG. 20.

According to various embodiments, the system 10 may provide disease information with a score value. For convenience of description, the disease information provided with a score will be referred to as a "disease score." Here, the disease score may be a probability value, but the present disclosure is not limited thereto. For example, the disease score provided by the analysis device 200 may be a probability value between 0 and 1. In one embodiment, the analysis device 200 may provide a probability value that the target is a skin cancer using an artificial neural network stored in the second memory 2020. Specifically, the second controller 2001 may input the pieces of spectrum data (e.g., the reference spectrum data and/or the target spectrum data) in the above-described embodiments as input data of the artificial neural network as it is or after processing the spectrum data, and the artificial neural network may calculate the input data to obtain the probability that the target in the suspicious tissue 2 is a skin cancer.

According to various embodiments, when the pulsed beam is radiated multiple times, the analysis device 200 may provide disease information on each of the targets. For example, when a probability value that a first target 4-a is a skin cancer is calculated to be 0.85, the analysis device 200 may provide first disease information 6-a through the output module 2060. Similarly, the analysis device 200 may provide second disease information 6-b and third disease information 6-c respectively on a second target 4-b and a third target 4-c. In some embodiments, the analysis device 200 may provide disease information only for a target having a probability value greater than or equal to a threshold value. For example, when the threshold value is 0.7, only the first disease information 6-a and the second disease information 6-b related to the first target 4-a and the second target 4-b, which have a probability value of 0.7 or higher, are provided to the user, and the third disease information 6-c having a probability value of less than 0.7 may not be output. However, this is merely an example, and another threshold value may be set, or all disease information may be output without the threshold value.

According to various embodiments, the analysis device 200 may provide a total score for one suspicious tissue. In one embodiment, when a plurality of pieces of disease information 6-a, 6-b, and 6-c are obtained for one suspicious tissue 2-a, the analysis device 200 may combine all or some of the plurality of pieces of disease information 6-a, 6-b, and 6-c in the same suspicious tissue 2-a to provide a total score TS1. When there are two or more separated suspicious tissues 2-b and 2-c, the suspicious tissues 2-b and 2-c may be provided with total scores TS2 and TS3, respectively. For example, the total score TS1 may be an average value of the plurality of pieces of disease information 6-a, 6-b, and 6-c. As another example, the total score TS1 may be selected as one piece of disease information (e.g., the first disease information 6-a) having the highest probability value among the plurality of pieces of disease information 6-a, 6-b, and 6-c. The probability of finding a skin cancer tissue may vary depending on the position even in the same suspicious tissue. Thus, when a total score is calculated on the basis of the pieces of disease information obtained from the plurality of targets 4-a, 4b, and 4-c in the same suspicious tissue 2-a, accuracy may be improved as compared to a case in which the disease information is obtained from one target (e.g., 4-a).

According to various embodiments, the analysis device 200 may tag the image, in which the guide light 3 is captured, with disease information and output the image tagged with the disease information. In one embodiment, the analysis device 200 may tag pieces of guide light 3-a, 3-b, and 3-c with the pieces of disease information 6-a, 6-b, and 6-c respectively corresponding thereto in the image, in which the guide light 3 is captured, and output the image. For example, the analysis device 200 may output an image in which first guide light 3-a is tagged with the first disease information 6-a, second guide light 3-b is tagged with the second disease information 6-b, and third guide light 3-c is tagged with the third disease information 6-c. In addition, the analysis device 200 may also output an image tagged with the total score TS1. As described above, when the plurality of suspicious tissues 2-b and 2-c exist in one image, the analysis device 200 may tag and provide the suspicious tissues 2-b and 2-c with the total scores TS2 and TS3 respectively corresponding thereto.

Figure 21:
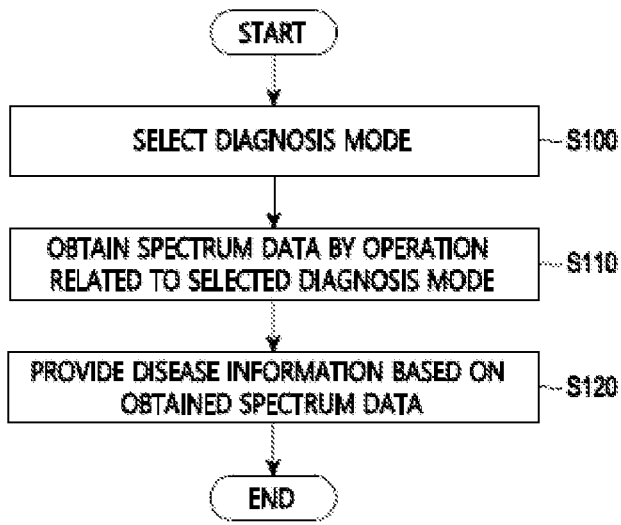
FIG. 21 is a flowchart of a disease information providing method according to still another embodiment.

FIG. 21 is a flowchart of a disease information providing method according to still another embodiment.

Referring to FIG. 21, the disease information providing method according to still another embodiment may include selecting a diagnosis mode (S100), obtaining spectrum data by an operation related to the selected diagnosis mode (S110), and providing disease information on the basis of the obtained spectrum data (S120). The disease information providing method of FIG. 21 may be combined with the above-described disease information providing methods according to various embodiments.

According to various embodiments, the system 10 may receive a diagnosis mode selection from a user (S100). In one embodiment, the analysis device 200 may provide two or more diagnosis modes to the user through the output module 2060, and the user may select one or more diagnosis modes through the input module 2040.

According to various embodiments, the diagnosis mode may be related to whether reference spectrum data is used. For example, the user may select the diagnosis mode to use or not use the reference spectrum data in receiving disease information. The system 10 may provide disease information on the basis of only target spectrum data without the reference spectrum data or provide the disease information using both the reference spectrum data and the target spectrum data, in response to the mode selection of the user.

According to various embodiments, the diagnosis mode may be related to the number of pieces of spectrum data used for disease information. For example, the user may determine the number of pieces of reference spectrum data and/or target spectrum data to be used in receiving the disease information. The system 10 may obtain one or a plurality of pieces of reference spectrum data and/or obtain one or a plurality of pieces of target spectrum data in response to the mode selection of the user, and provide the disease information on the basis thereof.

According to various embodiments, the system 10 may obtain spectrum data by an operation related to the input diagnosis mode (S110). The spectrum data obtaining operation performed in the system 10 is the same as or similar to the obtaining of spectrum data in the above-described embodiments, and thus a detailed description thereof will be omitted.

According to various embodiments, the system 10 may provide disease information on the basis of the obtained spectrum data (S120). The operation of providing the disease information is the same as or similar to those described in the above-described embodiments, and thus a detailed description thereof will be omitted.

The method according to the embodiment may be implemented in the form of program commands executable through various computer means and be recorded in a computer-readable medium. The computer-readable medium may include program instructions, data files, data structures, and the like in alone or a combination thereof. The program instructions recorded in the computer-readable medium may be specially designed and configured for the embodiment or may be effective to those skilled in the computer software. Examples of the computer-readable recording media include magnetic media such as a hard disk, a floppy disk, and a magnetic tape, optical recording media such as a compact disc read only memory (CD-ROM) and a digital versatile disc (DVD), a magneto-optical medium such as a floptical disk, and hardware devices specifically configured to store and execute program commands, such as a read only memory (ROM), a random access memory (RAM), a flash memory, and the like. Examples of the program instructions include machine language codes generated by a compiler, as well as high-level language codes which are executable by a computer using an interpreter or the like. The above-described hardware devices may be configured to operate as one or more software modules so as to perform an operation of the embodiment, and vice versa.

According to various embodiments, a disease information providing method may be provided, and the disease information providing method may include radiating first guide light, which guides a radiation position of a first pulsed beam, onto a suspicious tissue, receiving a first user input for instructing an output of the first pulsed beam while the first guide light is radiated, applying the first pulsed beam to the suspicious tissue to induce plasma ablation in a first target region corresponding to the radiation point of the first guide light, in response to the first user input, wherein the applying of the first pulsed beam is performed after obtaining first image data obtained by capturing an image of the first guide light and a tissue in a periphery the first guide light while the first guide light is radiated to the suspicious tissue, obtaining target spectrum data on the plasma ablation, obtaining first disease information related to the first target on the basis of the first spectrum data, and displaying the first image data and the first disease information.

According to one embodiment, the disease information providing method may further include generating a triggering signal by the user input, wherein the obtaining of the first image data and the applying of the pulsed beam are sequentially performed in response to the triggering signal.

According to one embodiment, the disease information providing method may further include obtaining reference spectrum data on a normal tissue adjacent to the suspicious tissue, wherein the obtaining of the reference spectrum data may include radiating second guide light, which guides a radiation position of a second pulsed beam, onto the normal tissue, receiving a second user input for instructing an output of the second pulsed beam while the second guide light is radiated, applying the second pulsed beam to the normal tissue to induce plasma ablation in a second target region corresponding to the radiation point of the second guide beam, in response to the second user input, and obtaining the reference spectrum data related to the plasma ablation.

According to one embodiment, in the obtaining of the first disease information, the first disease information may be obtained on the basis of both the reference spectrum data and the target spectrum data.

According to one embodiment, the obtaining of the first disease information may be performed using an artificial neural network trained by using training data labeled with previously obtained spectrum data and disease information.

According to one embodiment, the first disease information may include information on a probability that the suspicious tissue corresponding to the first target is a lesion tissue.

According to one embodiment, in the displaying of the first image data and the first disease information, the first image data and the first disease information may be merged and displayed.

According to one embodiment, the disease information providing method may include radiating third guide light, which guides a radiation position of a third pulsed beam, to a position different from the first target region on the suspicious tissue, receiving a third user input for instructing an output of the third pulsed beam while the third guide light is radiated, applying the third pulsed beam to the third target region to induce plasma ablation, in response to the third user input, wherein the applying of the third pulsed beam is performed after obtaining third image data obtained by capturing an image of the third guide light and a tissue in a periphery of the third guide light while the third guide light is radiated to the target, obtaining second target spectrum data related to the plasma ablation, and obtaining second disease information related to the second target region.

According to one embodiment, the obtaining of the first disease information may be performed on the basis of the first target spectrum data and the second target spectrum data, and the obtaining of the second disease information may be performed on the basis of the first target spectrum data and the second target spectrum data.

According to one embodiment, in the displaying of the first image data and the first disease information, the first guide light displayed on the first image data may be tagged with the first disease information and displayed.

According to one embodiment, the disease information providing method further includes outputting, in real time, an image capturing a radiation position of the first guide light before receiving the first user input.

According to various embodiments, a disease information providing device may be provided, and the disease information providing device may include a laser generating unit configured to generate a pulsed beam, a housing configured to accommodate the laser generating unit and including an opening providing a radiation path of the pulsed beam, a guide tip provided in a periphery of the opening and configured to adjust a radiation distance of the pulsed beam from a target to a laser generating module by being in contact with the target, a light receiving module disposed adjacent to the opening or the guide tip and is configured to receive plasma light induced when the pulsed beam is radiated to the target, a guide module disposed inside the housing and is configured to radiate guide light visually displaying a radiation position of the pulsed beam, an imaging module disposed in parallel with the light receiving module and is configured to capture an image of the radiation position of the pulsed beam and a predetermined region in a periphery of the radiation position, a switch module disposed on at least a part of an outer surface of the housing, and configured to trigger operations of the imaging module and the laser generating unit in response to a user input, and a processor configured to control operations of the laser generating module and the imaging module, wherein the processor is configured to, when the user input is applied to the switch module, transmit, to the imaging module, a first signal for instructing to capture an image of the guide light pointing at a radiation spot of the pulsed beam while the guide light is radiated, and after the first signal is transmitted, transmit a second signal for instructing the radiation of the pulsed beam to the target.

According to various embodiments, a disease information providing method may be provided, and the disease information providing method may include obtaining first spectrum data, wherein the obtaining of the first spectrum data may include radiating a first guide beam onto a suspicious tissue, obtaining first image data by capturing an image of at least a partial region of the suspicious tissue such that the first guide beam is included, after the capturing operation, outputting a first pulsed beam to a first target region corresponding to the first guide beam, and obtaining first spectrum data related to first plasma ablation induced in the first target region, obtaining second spectrum data, wherein the obtaining of the second spectrum data may include radiating a second guide beam onto the suspicious tissue, obtaining second image data by capturing an image of at least a partial region of the suspicious tissue such that the second guide beam is included, after the capturing operation, outputting a second pulsed beam to a second target region corresponding to the second guide beam, and obtaining second spectrum data related to second plasma ablation induced in the second target region, and obtaining a disease score for the suspicious tissue on the basis of the first spectrum data and the second spectrum data.

According to one embodiment, the disease score may reflect a probability value that the suspicious tissue is a disease tissue, and include a first disease score related to the first target region and a second disease score related to the second target region.

According to one embodiment, the disease score may be provided as an average of the first disease score and the second disease score.

According to one embodiment, one having a larger value of the first disease score and the second disease score may be selected as the disease score.

According to one embodiment, the disease information providing method may further include generating third image data by combining the first image data and the second image data, and tagging and displaying the third image data with the first disease score and the second disease score.

According to one embodiment, the disease information providing method may include obtaining reference spectrum data, wherein the obtaining of the reference spectrum data may include outputting a third pulsed beam to a reference region, wherein the reference region is at least a partial region of a normal tissue adjacent to the suspicious tissue, and obtaining reference spectrum data related to third plasma ablation induced in the reference region, and in the obtaining of the disease score, the disease score is obtained further on the basis of the reference spectrum data.

According to one embodiment, the obtaining of the reference spectrum data may further include radiating a third guide beam onto the normal tissue, and obtaining third image data by capturing an image of at least a partial region of the normal tissue such that the third guide beam is included.

According to one embodiment, the suspicious tissue may include a first suspicious tissue and a second suspicious tissue spaced apart from each other by a predetermined distance, the first spectrum data may be obtained from the first suspicious tissue, the second spectrum data may be obtained from the second suspicious tissue, and the reference spectrum data may be obtained from the normal tissue between the first suspicious tissue and the second suspicious tissue.

According to one embodiment, the suspicious tissue may be one physically divided lesion, and in the obtaining of the disease score, a comprehensive disease score for the one suspicious tissue may be obtained on the basis of both the first spectrum data and the second spectrum data.

According to one embodiment, the disease information providing method may further include receiving a mode selection, wherein, at least one of the number of target regions or the number of reference regions, which is required for obtaining the disease score, may be changed according to the mode selection.

According to various embodiments, accurate disease information on an object can be obtained by calculating a disease score for each of a plurality of pieces of spectrum data at different positions of the same object and comprehensively considering the scores.

According to various embodiments, image data, which is obtained by capturing an image of a guide beam guiding a radiation position of a pulsed beam, is provided before the pulsed beam is radiated, thereby allowing a user to clearly grasp the radiation position of the pulsed beam.

As is described above, while the present disclosure has been described with reference to the specific embodiments thereof, various changes and modification may be derived by those skilled in the art from the above description. For example, even when the described techniques may be performed in a different order than the described method, and/or elements of the described systems, structures, devices, circuits, and the like may be coupled to combined in other forms, or replaced or substituted by other components or equivalents, appropriate results can be achieved Therefore, other implementations, other embodiments, and equivalents to the appended claims fall within the scope of the following claims.

What is claimed is:

1. A disease information providing method performed by a disease information providing device, the method comprising:

obtaining first image including a first guide light pointing at a first spot on a suspicious tissue;

obtaining first spectrum data related to plasma ablation induced at the first spot;

obtaining first disease information related to the first spot based on the first spectrum data;

obtaining second image including a second guide light pointing at a second spot on the suspicious tissue;

obtaining second spectrum data related to plasma ablation induced at the second spot;

obtaining second disease information related to the second spot based on the second spectrum data;

calculating a comprehensive score as a single statistical value derived from the first disease information and the second disease information; and displaying a result image representing the suspicious tissue, wherein the displaying comprises:

tagging the first disease information to the first guide light in the result image, tagging the second disease information to the second guide light in the result image, and displaying the comprehensive score with the suspicious tissue in the result image.

2. The method of claim 1, wherein the calculating of the comprehensive score comprises calculating at least one of an average value, a maximum value, a mode value, or a median value of disease probabilities included in the first disease information and the second disease information.

3. The method of claim 1, wherein the tagging of the first disease information comprises displaying a numerical value representing a disease probability adjacent to the first guide light in the result image.

4. The method of claim 3, wherein the tagging of the first disease information comprises displaying a visual indicator having a color or a shape determined based on a value of the first disease information at a position corresponding to the first guide light.

5. The method of claim 1, wherein the obtaining of the first disease information is performed using an artificial neural network trained by using training data labeled with previously obtained spectrum data and disease information.

6. The method of claim 1, wherein the first disease information includes information on a probability that at least a part of the suspicious tissue corresponding to the first spot is a lesion tissue.

7. The method of claim 1, further comprising determining the suspicious tissue as a lesion tissue if the comprehensive score exceeds a preset threshold, and displaying a result of the determination in the result image.

\* \* \* \* \*